United States Patent
Balasubramanian et al.

(10) Patent No.: US 6,638,507 B1
(45) Date of Patent: Oct. 28, 2003

(54) MAMMALIAN PROTEASES; RELATED REAGENTS

(75) Inventors: Sriram Balasubramanian, La Jolla, CA (US); John Ford, Palo Alto, CA (US); Daniel M. Gorman, Newark, CA (US); Gerard Zurawski, San Juan Bautista, CA (US)

(73) Assignee: Schering Corporation, Kenilworth, NJ (US)

(*) Notice: Subject to any disclaimer, the term of this patent is extended or adjusted under 35 U.S.C. 154(b) by 0 days.

(21) Appl. No.: 09/650,284

(22) Filed: Aug. 29, 2000

Related U.S. Application Data

(62) Division of application No. 08/706,216, filed on Aug. 30, 1996, now Pat. No. 6,140,098.

(51) Int. Cl.[7] ............................................. A61K 39/395
(52) U.S. Cl. ........................ 424/146.1; 424/139.1; 530/387.9; 435/7.1; 435/810
(58) Field of Search ................. 530/387.9; 424/139.1, 424/146.1; 435/810, 7.1

(56) References Cited

U.S. PATENT DOCUMENTS 5,639,600 A * 6/1997 McGrath et al.
5,985,832 A 11/1999 Roodman et al.

OTHER PUBLICATIONS

Claudia Becker, et al., *Eur. J. Biochem.*, 228:456–462, 1995. "Purification, cDNA cloning and characterization of proteinase B, an asparagine-specific endopeptidase from germinating vetch (*Vica sativa* L.) seeds".

F. Bouillaud, *GenBank*, Accession No. R17110, , Jun. 12, 1996. Definition: "EST27c06 WATM1 *Homo sapiens* cDNA clone 27c06 similar to Proteawe. Homologous to pir IS31908IS31908 hemoglobinase—fluke (*Schistosoma japonicum*)".

Jing-May Chen, *J. of Biol. Chem.*, 272(12):8090–8098, Mar. 21, 1997. "Cloning, Isolation, and Characterization of Mammalian Legumain, an Asparaginyl Endopeptidase".

Thomas E. Creighton, *PROTEINS: Structures and Molecular Properties*, 2nd Ed., W.H. Freeman and Company, New York, New York, pp. 108, 109, 132 ans 133, 1993.

Alan H. Davis, et al., *J. Biol. Chem.*, 262:12851–12855, 1987. "Cloning and Gene Expression of *Schistosoma mansoni* Protease".

M. Ashraf el Meanawy, et al., *Am. J. Trop. Med. Hyg.*, 43:67–78, 1990. "Definition of the complete *Schistosoma mansoni* hemoglobinase mRNA sequence and gene expression in developing parasites".

Mitsuru Emi, et al., *Nature Genetics*, 5:151–157, 1993. "A novel metalloprotease/disintegrin-like gene at 17q21.3 is somatically rearranged in two primary breast cancers".

Genexpress, C. Auffray, et al., *GenBank*, Accession No. F01300, Sep. 21, 1995. Definition: "*H. sapiens* partial cDNA sequence; clone C6B02; version 1; strand (+), single read."

F.X. Gomis–Rüth, et al., *J. Mol. Bio.*, 239:513–544, 1994. "Refined 2·0 Å X–ray Crystal Structure of the Snake Venom. Zinc–endopeptidase Adamalysin II".

Todd W. Gusek, et al., *INFORM*, 2:14–18, 1991. "New protease identified for detergent use".

Gong–Ping He, et al., *Nature*, 378:92–96, 1995. "A eukaryotic transcriptional repressor with carboxypeptidase activity".

Yong–Keun Jung, et al., *Mol. Endocrinoligy*, 5:1257–1258, 1991. "Structural Characterization of the Rat Carboxypeptidase–E Gene".

T. Katagiri, et al., *Cytogenet Cell Genet*, 68:39–44, 1995. "Human metalloprotease/disintegrin–like (MDC) gene: exon–intron organization and alternative splicing".

Mo–Quen Klinkert, et al., *Molecular and Biochemical Parasitology*, 33:113–122, 1989. "Primary structures of Sm31/32 diagnostic proteins of *Schistosoma mansoni* and their identification of proteases".

Kazuyuki Kuroki, et al., *J. of Bio. Chem.* 15022–15028, 1995. "gb180, a Host Cell Glycoprotein That Binds Duck Hepatitis B Virus Particles, Is Encoded by a Member of the Carboxypeptidase Gene Family".

Edward Manser, et al., *Biochem J.*, 267:517–525, 1990. "Human carboxypeptidase E: Isolation and characterization of the cDNA, sequence conservation, expression and processing in vitro".

Denise A. Rowzarski, et al., *Structure*, 2:159–173, Mar. 15, 1994. "Structural comparison among the short–chain helical cytokines".

Hiroyuki Takeya, et al., *J. Biochem.*, 106:151–157, 1989. "Primary Structure of $H_2$–Proteinase, a Non–Hemorrhagic Metalloproteinase, Isolated from the Venom of the Habu Snake, *Trimeresurus flavoviridis*".

Seiji Yoshida, et al., *International Immunology*, 2:585–591, 1990 "Molecular cloning of cDNA encoding MS2 antigen, a novel cell surface antigen strongly expressed in murine monocytic lineage".

Coleman et al. (Research in Immunology, 1994; 145(1): 33–36).*

Abaza et al. (Journal of Protein Chemistry, vol. 11, No. 5, 1992, pp. 433–444).*

Lederman et al. (Molecular Immunology 28: 1171–1181, 1991).*

Li et al. (PNAS 77: 3211–3214, 1980).*

Ngo et al.; in The Protein Folding Problem and Tertiary Structure Prediction, 1994, Merz et al., (ed.), Birkhauser, Boston, MA, pp. 433 and 492–495.*

* cited by examiner

*Primary Examiner*—Patrick J. Nolan
(74) *Attorney, Agent, or Firm*—Edwin P. Ching; Tom Brody

(57) ABSTRACT

Nucleic acids encoding various proteases, from a mammal, reagents related thereto, including specific antibodies, and purified proteins are described. Methods of using said reagents and related diagnostic kits are also provided.

6 Claims, No Drawings

SEQUENCE LISTING

<160> NUMBER OF SEQ ID NOS: 7

<210> SEQ ID NO 1
<211> LENGTH: 2719
<212> TYPE: DNA
<213> ORGANISM: Homo sapiens
<220> FEATURE:
<221> NAME/KEY: CDS
<222> LOCATION: (337)..(2541)
<223> OTHER INFORMATION:

<400> SEQUENCE: 1

```
ttgatggcca ccaggtgatc tctggtctct tcagtgtggc tttgcagact ataaaggcgc      60
agcgcgccaa cgaggcgggt tggccccaga cggcggagag gaagggcaga gtcggcggtc     120
ctgagacttg gggcggcccc ttggaggtca gccccgctcg ctcctcccgg ccctctcctc     180
ctctccgagg tccgaggcgg gcagcgggct gtgggcgggc aggaggctgc ggaggggcgg     240
ggggcaggaa ggggcggggg gctcggcgca ctcggcagga agagaccgac ccgccacccg     300
ccgtagcccg cgcgcccctg gcactcaatc cccgcc atg tgg ggg ctc ctg ctc      354
                                        Met Trp Gly Leu Leu Leu
                                         1               5 gcc ctg gcc gcc ttc gcg ccg gcc gtc ggc ccg gct ctg ggg gcg ccc      402
Ala Leu Ala Ala Phe Ala Pro Ala Val Gly Pro Ala Leu Gly Ala Pro
             10                  15                  20 agg aac tcg gtg ctg ggc ctc gcg cag ccc ggg acc acc aag gtc cca      450
Arg Asn Ser Val Leu Gly Leu Ala Gln Pro Gly Thr Thr Lys Val Pro
         25                  30                  35 ggc tcg acc ccg gcc ctg cat agc agc ccg gca cag ccg ccg gcg gag      498
Gly Ser Thr Pro Ala Leu His Ser Ser Pro Ala Gln Pro Pro Ala Glu
     40                  45                  50 aca gct aac ggg acc tca gaa cag cat gtc cgg att cga gtc atc aag      546
Thr Ala Asn Gly Thr Ser Glu Gln His Val Arg Ile Arg Val Ile Lys
 55                  60                  65                  70 aag aaa aag gtc att atg aag aag cgg aag aag cta act cta act cgc      594
Lys Lys Lys Val Ile Met Lys Lys Arg Lys Lys Leu Thr Leu Thr Arg
                 75                  80                  85 ccc acc cca ctg gtg act gcc ggg ccc ctt gtg acc ccc act cca gca      642
Pro Thr Pro Leu Val Thr Ala Gly Pro Leu Val Thr Pro Thr Pro Ala
             90                  95                 100 ggg acc ctc gac ccc gct gag aaa caa gaa aca ggc tgt cct cct ttg      690
Gly Thr Leu Asp Pro Ala Glu Lys Gln Glu Thr Gly Cys Pro Pro Leu
        105                 110                 115 ggt ctg gag tcc ctg cga gtt tca gat agc cgg ctt gag gca tcc agc      738
Gly Leu Glu Ser Leu Arg Val Ser Asp Ser Arg Leu Glu Ala Ser Ser
    120                 125                 130 agc cag tcc ttt ggt ctt gga cca cac cga gga cgg ctc aac att cag      786
Ser Gln Ser Phe Gly Leu Gly Pro His Arg Gly Arg Leu Asn Ile Gln
135                 140                 145                 150 tca ggc ctg gag gac ggc gat cta tat gat gga gcc tgg tgt gct gag      834
Ser Gly Leu Glu Asp Gly Asp Leu Tyr Asp Gly Ala Trp Cys Ala Glu
                155                 160                 165
```

```
gag cag gac gcc gat cca tgg ttt cag gtg gac gct ggg cac ccc acc        882
Glu Gln Asp Ala Asp Pro Trp Phe Gln Val Asp Ala Gly His Pro Thr
            170                 175                 180 cgc ttc tcg ggt gtt atc aca cag ggc agg aac tct gtc tgg agg tat        930
Arg Phe Ser Gly Val Ile Thr Gln Gly Arg Asn Ser Val Trp Arg Tyr
        185                 190                 195 gac tgg gtc aca tca tac aag gtc cag ttc agc aat gac agt cgg acc        978
Asp Trp Val Thr Ser Tyr Lys Val Gln Phe Ser Asn Asp Ser Arg Thr
    200                 205                 210 tgg tgg gga agt agg aac cac agc agt ggg atg gac gca gta ttt cct       1026
Trp Trp Gly Ser Arg Asn His Ser Ser Gly Met Asp Ala Val Phe Pro
215                 220                 225                 230 gcc aat tca gac cca gaa act cca gtg ctg aac ctc ctg ccg gag ccc       1074
Ala Asn Ser Asp Pro Glu Thr Pro Val Leu Asn Leu Leu Pro Glu Pro
                235                 240                 245 cag gtg gcc cgc ttc att cgc ctg ctc ccc cag acc tgg ctc cag gga       1122
Gln Val Ala Arg Phe Ile Arg Leu Leu Pro Gln Thr Trp Leu Gln Gly
            250                 255                 260 ggc gcg cct tgc ctc cgg gca gag atc ctg gcc tgc cca gtc tca gac       1170
Gly Ala Pro Cys Leu Arg Ala Glu Ile Leu Ala Cys Pro Val Ser Asp
        265                 270                 275 ccc aat gac cta ttc ctt gag gcc cct gcg tcg gga tcc tct gac cct       1218
Pro Asn Asp Leu Phe Leu Glu Ala Pro Ala Ser Gly Ser Ser Asp Pro
    280                 285                 290 cta gac ttt cag cat cac aat tac aag gcc atg agg aag ctg atg aag       1266
Leu Asp Phe Gln His His Asn Tyr Lys Ala Met Arg Lys Leu Met Lys
295                 300                 305                 310 cag gta caa gag caa tgc ccc aac atc acc cgc atc tac agc att ggg       1314
Gln Val Gln Glu Gln Cys Pro Asn Ile Thr Arg Ile Tyr Ser Ile Gly
                315                 320                 325 aag agc tac cag ggc ctg aag ctg tat gtg atg gaa atg tcg gac aag       1362
Lys Ser Tyr Gln Gly Leu Lys Leu Tyr Val Met Glu Met Ser Asp Lys
            330                 335                 340 cct ggg gag cat gag ctg ggg gag cct gag gtg cgc tac gtg gct ggc       1410
Pro Gly Glu His Glu Leu Gly Glu Pro Glu Val Arg Tyr Val Ala Gly
        345                 350                 355 atg cat ggg aac gag gcc ctg ggg cgg gag ttg ctt ctg ctc ctg atg       1458
Met His Gly Asn Glu Ala Leu Gly Arg Glu Leu Leu Leu Leu Leu Met
    360                 365                 370 cag ttc ctg tgc cat gag ttc ctg cga ggg aac cca cag gtg acc cgg       1506
Gln Phe Leu Cys His Glu Phe Leu Arg Gly Asn Pro Gln Val Thr Arg
375                 380                 385                 390 ctg ctc tct gag atg cgc att cac ctg ctg ccc tcc atg aac cct gat       1554
Leu Leu Ser Glu Met Arg Ile His Leu Leu Pro Ser Met Asn Pro Asp
                395                 400                 405 ggc tat gag atc gcc tac cac cgg ggt tca gag ctg gtg ggc tgg gcc       1602
Gly Tyr Glu Ile Ala Tyr His Arg Gly Ser Glu Leu Val Gly Trp Ala
            410                 415                 420 gag ggc cgc tgg aac aac cag agc atc gat ctt aac cat aat ttt gct       1650
Glu Gly Arg Trp Asn Asn Gln Ser Ile Asp Leu Asn His Asn Phe Ala
        425                 430                 435 gac ctc aac aca cca ctg tgg gaa gca cag gac gat ggg aag gtg ccc       1698
Asp Leu Asn Thr Pro Leu Trp Glu Ala Gln Asp Asp Gly Lys Val Pro
    440                 445                 450 cac atc gtc ccc aac cat cac ctg cca ttg ccc act tac tac acc ctg       1746
His Ile Val Pro Asn His His Leu Pro Leu Pro Thr Tyr Tyr Thr Leu
455                 460                 465                 470 ccc aat gcc acc gtg gct cct gaa acg cgg gca gta atc aag tgg atg       1794
Pro Asn Ala Thr Val Ala Pro Glu Thr Arg Ala Val Ile Lys Trp Met
```

-continued

| | | | | |
|---|---|---|---|---|
| | 475 | 480 | 485 | |
| aag cgg atc ccc ttt gtg cta agt gcc aac ctc cac ggg ggt gag ctc<br>Lys Arg Ile Pro Phe Val Leu Ser Ala Asn Leu His Gly Gly Glu Leu<br>490 495 500 | | | | 1842 |
| gtg gtg tcc tac cca ttc gac atg act cgc acc ccg tgg gct gcc cgc<br>Val Val Ser Tyr Pro Phe Asp Met Thr Arg Thr Pro Trp Ala Ala Arg<br>505 510 515 | | | | 1890 |
| gag ctc acg ccc aca cca gat gat gct gtg ttt cgc tgg ctc agc act<br>Glu Leu Thr Pro Thr Pro Asp Asp Ala Val Phe Arg Trp Leu Ser Thr<br>520 525 530 | | | | 1938 |
| gtc tat gct ggc agt aat ctg gcc atg cag gac acc agc cgc cga ccc<br>Val Tyr Ala Gly Ser Asn Leu Ala Met Gln Asp Thr Ser Arg Arg Pro<br>535 540 545 550 | | | | 1986 |
| tgc cac agc cag gac ttc tcc gtg cac ggc aac atc atc aac ggg gct<br>Cys His Ser Gln Asp Phe Ser Val His Gly Asn Ile Ile Asn Gly Ala<br>555 560 565 | | | | 2034 |
| gac tgg cac acg gtc ccc ggg agc atg aat gac ttc agc tac cta cac<br>Asp Trp His Thr Val Pro Gly Ser Met Asn Asp Phe Ser Tyr Leu His<br>570 575 580 | | | | 2082 |
| acc aac tgc ttt gag gtc act gtg gag ctg tcc tgt gac aag ttc cct<br>Thr Asn Cys Phe Glu Val Thr Val Glu Leu Ser Cys Asp Lys Phe Pro<br>585 590 595 | | | | 2130 |
| cac gag aat gaa ttg ccc cag gag tgg gag aac aac aaa gac gcc ctc<br>His Glu Asn Glu Leu Pro Gln Glu Trp Glu Asn Asn Lys Asp Ala Leu<br>600 605 610 | | | | 2178 |
| ctc acc tac ctg gag cag gtg cgc atg ggc att gca gga gtg gtg agg<br>Leu Thr Tyr Leu Glu Gln Val Arg Met Gly Ile Ala Gly Val Val Arg<br>615 620 625 630 | | | | 2226 |
| gac aag gac acg gag ctt ggg att gct gac gct gtc att gcc gtg gat<br>Asp Lys Asp Thr Glu Leu Gly Ile Ala Asp Ala Val Ile Ala Val Asp<br>635 640 645 | | | | 2274 |
| ggg att aac cat gac gtg acc acg gcg tgg ggc ggg gat tat tgg cgt<br>Gly Ile Asn His Asp Val Thr Thr Ala Trp Gly Gly Asp Tyr Trp Arg<br>650 655 660 | | | | 2322 |
| ctg ctg acc cca ggg gac tac atg gtg act gcc agt gcc gag ggc tac<br>Leu Leu Thr Pro Gly Asp Tyr Met Val Thr Ala Ser Ala Glu Gly Tyr<br>665 670 675 | | | | 2370 |
| cat tca gtg aca cgg aac tgt cgg gtc acc ttt gaa gag ggc ccc ttc<br>His Ser Val Thr Arg Asn Cys Arg Val Thr Phe Glu Glu Gly Pro Phe<br>680 685 690 | | | | 2418 |
| ccc tgc aat ttc gtg ctc acc aag act ccc aaa cag agg ctg cgc gag<br>Pro Cys Asn Phe Val Leu Thr Lys Thr Pro Lys Gln Arg Leu Arg Glu<br>695 700 705 710 | | | | 2466 |
| ctg ctg gca gct ggg gcc aag gtg ccc ccg gac ctt cgc agg cgc ctg<br>Leu Leu Ala Ala Gly Ala Lys Val Pro Pro Asp Leu Arg Arg Arg Leu<br>715 720 725 | | | | 2514 |
| gag cgg cta agg gga cag aag gat tga tacctgcggt ttaagagccc<br>Glu Arg Leu Arg Gly Gln Lys Asp<br>730 | | | | 2561 |
| tagggcaggc tggacctgtc aagacgggaa ggggaagagt agagagggag ggacaaagtg | | | | 2621 |
| aggaaaaggt gctcattaaa gctaccggc accttaaaaa aaaaaaaaaa aaaaaaaaa | | | | 2681 |
| aaaaaaaaaa aaaaaaaaaa aaaaaagggg cggccgct | | | | 2719 |

<210> SEQ ID NO 2
<211> LENGTH: 734
<212> TYPE: PRT
<213> ORGANISM: Homo sapiens

<400> SEQUENCE: 2

-continued

```
Met Trp Gly Leu Leu Leu Ala Leu Ala Ala Phe Ala Pro Ala Val Gly
1               5                   10                  15

Pro Ala Leu Gly Ala Pro Arg Asn Ser Val Leu Gly Leu Ala Gln Pro
            20                  25                  30

Gly Thr Thr Lys Val Pro Gly Ser Thr Pro Ala Leu His Ser Ser Pro
        35                  40                  45

Ala Gln Pro Pro Ala Glu Thr Ala Asn Gly Thr Ser Glu Gln His Val
    50                  55                  60

Arg Ile Arg Val Ile Lys Lys Lys Val Ile Met Lys Lys Arg Lys
65                  70                  75                  80

Lys Leu Thr Leu Thr Arg Pro Thr Pro Leu Val Thr Ala Gly Pro Leu
                85                  90                  95

Val Thr Pro Thr Pro Ala Gly Thr Leu Asp Pro Ala Glu Lys Gln Glu
            100                 105                 110

Thr Gly Cys Pro Pro Leu Gly Leu Glu Ser Leu Arg Val Ser Asp Ser
        115                 120                 125

Arg Leu Glu Ala Ser Ser Gln Ser Phe Gly Leu Gly Pro His Arg
    130                 135                 140

Gly Arg Leu Asn Ile Gln Ser Gly Leu Glu Asp Gly Asp Leu Tyr Asp
145                 150                 155                 160

Gly Ala Trp Cys Ala Glu Glu Gln Asp Ala Asp Pro Trp Phe Gln Val
            165                 170                 175

Asp Ala Gly His Pro Thr Arg Phe Ser Gly Val Ile Thr Gln Gly Arg
            180                 185                 190

Asn Ser Val Trp Arg Tyr Asp Trp Val Thr Ser Tyr Lys Val Gln Phe
        195                 200                 205

Ser Asn Asp Ser Arg Thr Trp Trp Gly Ser Arg Asn His Ser Ser Gly
    210                 215                 220

Met Asp Ala Val Phe Pro Ala Asn Ser Asp Pro Glu Thr Pro Val Leu
225                 230                 235                 240

Asn Leu Leu Pro Glu Pro Gln Val Ala Arg Phe Ile Arg Leu Leu Pro
            245                 250                 255

Gln Thr Trp Leu Gln Gly Gly Ala Pro Cys Leu Arg Ala Glu Ile Leu
            260                 265                 270

Ala Cys Pro Val Ser Asp Pro Asn Asp Leu Phe Leu Glu Ala Pro Ala
        275                 280                 285

Ser Gly Ser Ser Asp Pro Leu Asp Phe Gln His His Asn Tyr Lys Ala
    290                 295                 300

Met Arg Lys Leu Met Lys Gln Val Gln Glu Gln Cys Pro Asn Ile Thr
305                 310                 315                 320

Arg Ile Tyr Ser Ile Gly Lys Ser Tyr Gln Gly Leu Lys Leu Tyr Val
            325                 330                 335

Met Glu Met Ser Asp Lys Pro Gly Glu His Glu Leu Gly Glu Pro Glu
            340                 345                 350

Val Arg Tyr Val Ala Gly Met His Gly Asn Glu Ala Leu Gly Arg Glu
        355                 360                 365

Leu Leu Leu Leu Leu Met Gln Phe Leu Cys His Glu Phe Leu Arg Gly
    370                 375                 380

Asn Pro Gln Val Thr Arg Leu Leu Ser Glu Met Arg Ile His Leu Leu
385                 390                 395                 400

Pro Ser Met Asn Pro Asp Gly Tyr Glu Ile Ala Tyr His Arg Gly Ser
            405                 410                 415
```

```
Glu Leu Val Gly Trp Ala Glu Gly Arg Trp Asn Asn Gln Ser Ile Asp
            420                 425                 430

Leu Asn His Asn Phe Ala Asp Leu Asn Thr Pro Leu Trp Glu Ala Gln
        435                 440                 445

Asp Asp Gly Lys Val Pro His Ile Val Pro Asn His His Leu Pro Leu
    450                 455                 460

Pro Thr Tyr Tyr Thr Leu Pro Asn Ala Thr Val Ala Pro Glu Thr Arg
465                 470                 475                 480

Ala Val Ile Lys Trp Met Lys Arg Ile Pro Phe Val Leu Ser Ala Asn
                485                 490                 495

Leu His Gly Gly Glu Leu Val Val Ser Tyr Pro Phe Asp Met Thr Arg
            500                 505                 510

Thr Pro Trp Ala Ala Arg Glu Leu Thr Pro Thr Pro Asp Asp Ala Val
        515                 520                 525

Phe Arg Trp Leu Ser Thr Val Tyr Ala Gly Ser Asn Leu Ala Met Gln
530                 535                 540

Asp Thr Ser Arg Arg Pro Cys His Ser Gln Asp Phe Ser Val His Gly
545                 550                 555                 560

Asn Ile Ile Asn Gly Ala Asp Trp His Thr Val Pro Gly Ser Met Asn
                565                 570                 575

Asp Phe Ser Tyr Leu His Thr Asn Cys Phe Glu Val Thr Val Glu Leu
            580                 585                 590

Ser Cys Asp Lys Phe Pro His Glu Asn Glu Leu Pro Gln Glu Trp Glu
        595                 600                 605

Asn Asn Lys Asp Ala Leu Leu Thr Tyr Leu Glu Gln Val Arg Met Gly
610                 615                 620

Ile Ala Gly Val Val Arg Asp Lys Asp Thr Glu Leu Gly Ile Ala Asp
625                 630                 635                 640

Ala Val Ile Ala Val Asp Gly Ile Asn His Asp Val Thr Thr Ala Trp
                645                 650                 655

Gly Gly Asp Tyr Trp Arg Leu Leu Thr Pro Gly Asp Tyr Met Val Thr
            660                 665                 670

Ala Ser Ala Glu Gly Tyr His Ser Val Thr Arg Asn Cys Arg Val Thr
        675                 680                 685

Phe Glu Glu Gly Pro Phe Pro Cys Asn Phe Val Leu Thr Lys Thr Pro
690                 695                 700

Lys Gln Arg Leu Arg Glu Leu Leu Ala Ala Gly Ala Lys Val Pro Pro
705                 710                 715                 720

Asp Leu Arg Arg Arg Leu Glu Arg Leu Arg Gly Gln Lys Asp
                725                 730

<210> SEQ ID NO 3
<211> LENGTH: 2030
<212> TYPE: DNA
<213> ORGANISM: Homo sapiens
<220> FEATURE:
<221> NAME/KEY: CDS
<222> LOCATION: (183)..(1484)
<223> OTHER INFORMATION:

<400> SEQUENCE: 3
caggtaccgg tccggaattc ccgggtcgac ccacgcgtcc ggtttggtgt gaggctgcga     60
gccgccgcga gttctcacgg tcccgccggc gccaccaccg cggtcactca ccgccgccgc    120
cgccaccact gccaccacgg tcgcctgcca caggtgtctg caattgaact ccaaggtgca    180 ga atg gtt tgg aaa gta gct gta ttc ctc agt gtg gcc ctg ggc att      227
```

```
    Met Val Trp Lys Val Ala Val Phe Leu Ser Val Ala Leu Gly Ile
     1               5                  10                 15 ggt gcc gtt cct ata gat gat cct gaa gat gga ggc aag cac tgg gtg       275
Gly Ala Val Pro Ile Asp Asp Pro Glu Asp Gly Gly Lys His Trp Val
                 20                  25                  30 gtg atc gtg gca ggt tca aat ggc tgg tat aat tat agg cac cag gca       323
Val Ile Val Ala Gly Ser Asn Gly Trp Tyr Asn Tyr Arg His Gln Ala
             35                  40                  45 gac gcg tgc cat gcc tac cag atc att cac cgc aat ggg att cct gac       371
Asp Ala Cys His Ala Tyr Gln Ile Ile His Arg Asn Gly Ile Pro Asp
         50                  55                  60 gaa cag atc gtt gtg atg atg tac gat gac att gct tac tct gaa gac       419
Glu Gln Ile Val Val Met Met Tyr Asp Asp Ile Ala Tyr Ser Glu Asp
 65                  70                  75 aat ccc act cca gga att gtg atc aac agg ccc aat ggc aca gat gtc       467
Asn Pro Thr Pro Gly Ile Val Ile Asn Arg Pro Asn Gly Thr Asp Val
 80                  85                  90                  95 tat cag gga gtc ccg aag gac tac act gga gag gat gtt acc cca caa       515
Tyr Gln Gly Val Pro Lys Asp Tyr Thr Gly Glu Asp Val Thr Pro Gln
                100                 105                 110 aat ttc ctt gct gtg ttg aga ggc gat gca gaa gca gtg aag ggc ata       563
Asn Phe Leu Ala Val Leu Arg Gly Asp Ala Glu Ala Val Lys Gly Ile
            115                 120                 125 gga tcc ggc aaa gtc ctg aag agt ggc ccc cag gat cac gtg ttc att       611
Gly Ser Gly Lys Val Leu Lys Ser Gly Pro Gln Asp His Val Phe Ile
        130                 135                 140 tac ttc act gac cat gga tct act gga ata ctg gtt ttt ccc aat gaa       659
Tyr Phe Thr Asp His Gly Ser Thr Gly Ile Leu Val Phe Pro Asn Glu
    145                 150                 155 gat ctt cat gta aag gac ctg aat gag acc atc cat tac atg tac aaa       707
Asp Leu His Val Lys Asp Leu Asn Glu Thr Ile His Tyr Met Tyr Lys
160                 165                 170                 175 cac aaa atg tac cga aag atg gtg ttc tac att gaa gcc tgt gag tct       755
His Lys Met Tyr Arg Lys Met Val Phe Tyr Ile Glu Ala Cys Glu Ser
                180                 185                 190 ggg tcc atg atg aac cac ctg ccg gat aac atc aat gtt tat gca act       803
Gly Ser Met Met Asn His Leu Pro Asp Asn Ile Asn Val Tyr Ala Thr
            195                 200                 205 act gct gcc aac ccc aga gag tcg tcc tac gcc tgt tac tat gat gag       851
Thr Ala Ala Asn Pro Arg Glu Ser Ser Tyr Ala Cys Tyr Tyr Asp Glu
        210                 215                 220 aag agg tcc acg tac ctg ggg gac tgg tac agc gtc aac tgg atg gaa       899
Lys Arg Ser Thr Tyr Leu Gly Asp Trp Tyr Ser Val Asn Trp Met Glu
    225                 230                 235 gac tcg gac gtg gaa gat ctg act aaa gag acc ctg cac aag cag tac       947
Asp Ser Asp Val Glu Asp Leu Thr Lys Glu Thr Leu His Lys Gln Tyr
240                 245                 250                 255 cac ctg gta aaa tcg cac acc aac acc agc cac gtc atg cag tat gga       995
His Leu Val Lys Ser His Thr Asn Thr Ser His Val Met Gln Tyr Gly
                260                 265                 270 aac aaa aca atc tcc acc atg aaa gtg atg cag ttt cag ggt atg aaa      1043
Asn Lys Thr Ile Ser Thr Met Lys Val Met Gln Phe Gln Gly Met Lys
            275                 280                 285 cgc aaa gcc agt tct ccc gtc ccc cta cct cca gtc aca cac ctt gac      1091
Arg Lys Ala Ser Ser Pro Val Pro Leu Pro Pro Val Thr His Leu Asp
        290                 295                 300 ctc acc ccc agc cct gat gtg cct ctc acc atc atg aaa agg aaa ctg      1139
Leu Thr Pro Ser Pro Asp Val Pro Leu Thr Ile Met Lys Arg Lys Leu
    305                 310                 315
```

-continued

| | | |
|---|---|---|
| atg aac acc aat gat ctg gag gag tcc agg cag ctc acg gag gag atc<br>Met Asn Thr Asn Asp Leu Glu Glu Ser Arg Gln Leu Thr Glu Glu Ile<br>320                        325                      330                      335 | 1187 |
| cag cgg cat ctg gat gcc agg cac ctc att gag aag tca gtg cgt aag<br>Gln Arg His Leu Asp Ala Arg His Leu Ile Glu Lys Ser Val Arg Lys<br>                    340                      345                      350 | 1235 |
| atc gtc tcc ttg ctg gca gcg tcc gag gct gag gtg gag cag ctc ctg<br>Ile Val Ser Leu Leu Ala Ala Ser Glu Ala Glu Val Glu Gln Leu Leu<br>355                                  360                      365 | 1283 |
| tcc gag aga gcc ccg ctc acg ggg cac agc tgc tac cca gag gcc ctg<br>Ser Glu Arg Ala Pro Leu Thr Gly His Ser Cys Tyr Pro Glu Ala Leu<br>            370                      375                      380 | 1331 |
| ctg cac ttc cgg acc cac tgc ttc aac tgg cac tcc ccc acg tac gag<br>Leu His Phe Arg Thr His Cys Phe Asn Trp His Ser Pro Thr Tyr Glu<br>385                                  390                      395 | 1379 |
| tat gcg ttg aga cat ttg tac gtg ctg gtc aac ctt tgt gag aag ccg<br>Tyr Ala Leu Arg His Leu Tyr Val Leu Val Asn Leu Cys Glu Lys Pro<br>400                        405                      410                      415 | 1427 |
| tat cca ctt cac agg ata aaa ttg tcc atg gac cac gtg tgc ctt ggt<br>Tyr Pro Leu His Arg Ile Lys Leu Ser Met Asp His Val Cys Leu Gly<br>            420                      425                      430 | 1475 |
| cac tac tga agagctgcct cctggaagct tttccaagtg tgagcgcccc<br>His Tyr | 1524 |
| cccgactgtg tgctgatcag agactggaga ggtggagtga aagtctccg ctgctcgggc | 1584 |
| cctcctgggg agccccgct ccagggctcg ctccaggacc ttcttcacaa gatgacttgc | 1644 |
| tcgctgttac ctgcttcccc agtctttct gaaaaactac aaattagggt gggaaaagct | 1704 |
| ctgtattgag aagggtcata tttgctttct aggaggtttg ttgttttgcc tgttagtttt | 1764 |
| gaggagcagg aagctcatgg gggcttctgt agccctctc aaaaggagtc tttattctga | 1824 |
| gaatttgaag ctgaaacctc tttaaatttt cagaatgatt ttattgaaga gggccgcaag | 1884 |
| ccccaaatgg aaaactgttt ttagaaaata tgatgatttt tgattgcttt tgtatttaat | 1944 |
| tctgcaggtg ttcaagtctt aaaaaataaa gatttataac agaacccaaa aaaaaaaaa | 2004 |
| aaaaaaaaaa aaaaagggc ggccgc | 2030 |

<210> SEQ ID NO 4
<211> LENGTH: 433
<212> TYPE: PRT
<213> ORGANISM: Homo sapiens

<400> SEQUENCE: 4

Met Val Trp Lys Val Ala Val Phe Leu Ser Val Ala Leu Gly Ile Gly
1               5                   10                  15

Ala Val Pro Ile Asp Asp Pro Glu Asp Gly Gly Lys His Trp Val Val
                20                  25                  30

Ile Val Ala Gly Ser Asn Gly Trp Tyr Asn Tyr Arg His Gln Ala Asp
            35                  40                  45

Ala Cys His Ala Tyr Gln Ile Ile His Arg Asn Gly Ile Pro Asp Glu
        50                  55                  60

Gln Ile Val Val Met Met Tyr Asp Asp Ile Ala Tyr Ser Glu Asp Asn
65                  70                  75                  80

Pro Thr Pro Gly Ile Val Ile Asn Arg Pro Asn Gly Thr Asp Val Tyr
                85                  90                  95

Gln Gly Val Pro Lys Asp Tyr Thr Gly Glu Asp Val Thr Pro Gln Asn
            100                 105                 110

Phe Leu Ala Val Leu Arg Gly Asp Ala Glu Ala Val Lys Gly Ile Gly

```
                    115                 120                 125
Ser Gly Lys Val Leu Lys Ser Gly Pro Gln Asp His Val Phe Ile Tyr
    130                 135                 140

Phe Thr Asp His Gly Ser Thr Gly Ile Leu Val Phe Pro Asn Glu Asp
145                 150                 155                 160

Leu His Val Lys Asp Leu Asn Glu Thr Ile His Tyr Met Tyr Lys His
                165                 170                 175

Lys Met Tyr Arg Lys Met Val Phe Tyr Ile Glu Ala Cys Glu Ser Gly
                180                 185                 190

Ser Met Met Asn His Leu Pro Asp Asn Ile Asn Val Tyr Ala Thr Thr
            195                 200                 205

Ala Ala Asn Pro Arg Glu Ser Ser Tyr Ala Cys Tyr Tyr Asp Glu Lys
            210                 215                 220

Arg Ser Thr Tyr Leu Gly Asp Trp Tyr Ser Val Asn Trp Met Glu Asp
225                 230                 235                 240

Ser Asp Val Glu Asp Leu Thr Lys Glu Thr Leu His Lys Gln Tyr His
                245                 250                 255

Leu Val Lys Ser His Thr Asn Thr Ser His Val Met Gln Tyr Gly Asn
            260                 265                 270

Lys Thr Ile Ser Thr Met Lys Val Met Gln Phe Gln Gly Met Lys Arg
            275                 280                 285

Lys Ala Ser Ser Pro Val Pro Leu Pro Pro Val Thr His Leu Asp Leu
290                 295                 300

Thr Pro Ser Pro Asp Val Pro Leu Thr Ile Met Lys Arg Lys Leu Met
305                 310                 315                 320

Asn Thr Asn Asp Leu Glu Glu Ser Arg Gln Leu Thr Glu Glu Ile Gln
                325                 330                 335

Arg His Leu Asp Ala Arg His Leu Ile Glu Lys Ser Val Arg Lys Ile
                340                 345                 350

Val Ser Leu Leu Ala Ala Ser Glu Ala Glu Val Glu Gln Leu Leu Ser
            355                 360                 365

Glu Arg Ala Pro Leu Thr Gly His Ser Cys Tyr Pro Glu Ala Leu Leu
            370                 375                 380

His Phe Arg Thr His Cys Phe Asn Trp His Ser Pro Thr Tyr Glu Tyr
385                 390                 395                 400

Ala Leu Arg His Leu Tyr Val Leu Val Asn Leu Cys Glu Lys Pro Tyr
                405                 410                 415

Pro Leu His Arg Ile Lys Leu Ser Met Asp His Val Cys Leu Gly His
                420                 425                 430

Tyr

<210> SEQ ID NO 5
<211> LENGTH: 1173
<212> TYPE: DNA
<213> ORGANISM: Homo sapiens
<220> FEATURE:
<221> NAME/KEY: CDS
<222> LOCATION: (1)..(1173)
<223> OTHER INFORMATION:

<400> SEQUENCE: 5 atg cgc ggt ctc ggg ctc tgg ctg ctg ggc gcg atg atg ctg cct gcg      48
Met Arg Gly Leu Gly Leu Trp Leu Leu Gly Ala Met Met Leu Pro Ala
1               5                   10                  15 att gcc ccc agc cgg ccc tgg gcc ctc atg gag cag tat gag gtc gtg      96
Ile Ala Pro Ser Arg Pro Trp Ala Leu Met Glu Gln Tyr Glu Val Val
```

-continued

| | | | | | | | |
|---|---|---|---|---|---|---|---|
| | | 20 | | 25 | | 30 | | ttg ccg cgg tgt ctg cca ggc ccc cga gtc cgc cga gct ctg ccc tcc       144
Leu Pro Arg Cys Leu Pro Gly Pro Arg Val Arg Arg Ala Leu Pro Ser
         35              40              45 cac ttg ggc ctg cac cca gag agg gtg agc tac gtc ctt ggg gcc aca       192
His Leu Gly Leu His Pro Glu Arg Val Ser Tyr Val Leu Gly Ala Thr
    50              55              60 ggg cac aac ttc acc ctc cac ctg cgg aag aac agg gac ctg ctg ggt       240
Gly His Asn Phe Thr Leu His Leu Arg Lys Asn Arg Asp Leu Leu Gly
65              70              75              80 tcc ggc tac aca gag acc tat acg gct gcc aat ggc tcc gag gtg acg       288
Ser Gly Tyr Thr Glu Thr Tyr Thr Ala Ala Asn Gly Ser Glu Val Thr
            85              90              95 gag cag cct cgc ggg cag gac cac tgc ttc tac cag ggc cac gta gag       336
Glu Gln Pro Arg Gly Gln Asp His Cys Phe Tyr Gln Gly His Val Glu
            100             105             110 ggg tac ccg gac tca gcc gcc agc ctc agc acc tgt gcc ggc ctc agg       384
Gly Tyr Pro Asp Ser Ala Ala Ser Leu Ser Thr Cys Ala Gly Leu Arg
            115             120             125 ggt ttc ttc cag gtg ggg tca gac ctg cac ctg atc gag ccc ctg gat       432
Gly Phe Phe Gln Val Gly Ser Asp Leu His Leu Ile Glu Pro Leu Asp
    130             135             140 gaa ggt ggc gag ggc gga cgg cac gcc gtg tac cag gct gag cac ctg       480
Glu Gly Gly Glu Gly Gly Arg His Ala Val Tyr Gln Ala Glu His Leu
145             150             155             160 ctg cag acg gcc ggg acc tgc ggg gtc agc gac gac agc ctg ggc agc       528
Leu Gln Thr Ala Gly Thr Cys Gly Val Ser Asp Asp Ser Leu Gly Ser
            165             170             175 ctc ctg gga ccc cgg acg gca gcc gtc ttc agg cct cgg ccc ggg gac       576
Leu Leu Gly Pro Arg Thr Ala Ala Val Phe Arg Pro Arg Pro Gly Asp
            180             185             190 tct ctg cca tcc cga gag acc cgc tac gtg gag ctg tat gtg gtc gtg       624
Ser Leu Pro Ser Arg Glu Thr Arg Tyr Val Glu Leu Tyr Val Val Val
            195             200             205 gac aat gca gag ttc cag atg ctg ggg agc gaa gca gcc gtg cgt cat       672
Asp Asn Ala Glu Phe Gln Met Leu Gly Ser Glu Ala Ala Val Arg His
    210             215             220 cgg gtg ctg gag gtg gtg aat cac gtg gac aag cta tat cag aaa ctc       720
Arg Val Leu Glu Val Val Asn His Val Asp Lys Leu Tyr Gln Lys Leu
225             230             235             240 aac ttc cgt gtg gtc ctg gtg ggc ctg gag att tgg aat agt cag gac       768
Asn Phe Arg Val Val Leu Val Gly Leu Glu Ile Trp Asn Ser Gln Asp
            245             250             255 agg ttc cac gtc agc ccc gac ccc agt gtc aca ctg gag aac ctc ctg       816
Arg Phe His Val Ser Pro Asp Pro Ser Val Thr Leu Glu Asn Leu Leu
            260             265             270 acc tgg cag gca cgg caa cgg aca cgg cgg cac ctg cat gac aac gta       864
Thr Trp Gln Ala Arg Gln Arg Thr Arg Arg His Leu His Asp Asn Val
    275             280             285 cag ctc atc acg ggt gtc gac ttc acc ggg act act gtg ggg ttt gcc       912
Gln Leu Ile Thr Gly Val Asp Phe Thr Gly Thr Thr Val Gly Phe Ala
    290             295             300 agg gtg tcc gcc atg tgc tcc cac agc tca ggg gct gtg aac cag gac       960
Arg Val Ser Ala Met Cys Ser His Ser Ser Gly Ala Val Asn Gln Asp
305             310             315             320 cac agc aag aac ccc gtg ggc gtg gct gca cca tgg ccc atg aga tgg      1008
His Ser Lys Asn Pro Val Gly Val Ala Ala Pro Trp Pro Met Arg Trp
            325             330             335 gcc aca acc tgg gca tgg acc atg atg aga acg tcc agg gct gcc gct      1056

```
Ala Thr Thr Trp Ala Trp Thr Met Met Arg Thr Ser Arg Ala Ala Ala
                340                 345                 350 gcc agg aac gct tcg agg ccg gcc gct gca tca tgg cag gca gca ttg      1104
Ala Arg Asn Ala Ser Arg Pro Ala Ala Ser Trp Gln Ala Ala Leu
            355                 360                 365 gct cca gtt tcc cca gga tgt tca gtg act gca gcc agg cct acc tgg      1152
Ala Pro Val Ser Pro Gly Cys Ser Val Thr Ala Ala Arg Pro Thr Trp
370                 375                 380 aga gct ttt tgg agc ggc cgc                                          1173
Arg Ala Phe Trp Ser Gly Arg
385                 390
```

<210> SEQ ID NO 6
<211> LENGTH: 391
<212> TYPE: PRT
<213> ORGANISM: Homo sapiens

<400> SEQUENCE: 6

```
Met Arg Gly Leu Gly Leu Trp Leu Leu Gly Ala Met Met Leu Pro Ala
1               5                   10                  15

Ile Ala Pro Ser Arg Pro Trp Ala Leu Met Glu Gln Tyr Glu Val Val
                20                  25                  30

Leu Pro Arg Cys Leu Pro Gly Pro Arg Val Arg Arg Ala Leu Pro Ser
            35                  40                  45

His Leu Gly Leu His Pro Glu Arg Val Ser Tyr Val Leu Gly Ala Thr
        50                  55                  60

Gly His Asn Phe Thr Leu His Leu Arg Lys Asn Arg Asp Leu Leu Gly
65                  70                  75                  80

Ser Gly Tyr Thr Glu Thr Tyr Thr Ala Ala Asn Gly Ser Glu Val Thr
                85                  90                  95

Glu Gln Pro Arg Gly Gln Asp His Cys Phe Tyr Gln Gly His Val Glu
            100                 105                 110

Gly Tyr Pro Asp Ser Ala Ala Ser Leu Ser Thr Cys Ala Gly Leu Arg
        115                 120                 125

Gly Phe Phe Gln Val Gly Ser Asp Leu His Leu Ile Glu Pro Leu Asp
    130                 135                 140

Glu Gly Gly Glu Gly Gly Arg His Ala Val Tyr Gln Ala Glu His Leu
145                 150                 155                 160

Leu Gln Thr Ala Gly Thr Cys Gly Val Ser Asp Asp Ser Leu Gly Ser
                165                 170                 175

Leu Leu Gly Pro Arg Thr Ala Ala Val Phe Arg Pro Arg Pro Gly Asp
            180                 185                 190

Ser Leu Pro Ser Arg Glu Thr Arg Tyr Val Glu Leu Tyr Val Val Val
        195                 200                 205

Asp Asn Ala Glu Phe Gln Met Leu Gly Ser Glu Ala Ala Val Arg His
    210                 215                 220

Arg Val Leu Glu Val Val Asn His Val Asp Lys Leu Tyr Gln Lys Leu
225                 230                 235                 240

Asn Phe Arg Val Val Leu Val Gly Leu Glu Ile Trp Asn Ser Gln Asp
                245                 250                 255

Arg Phe His Val Ser Pro Asp Pro Ser Val Thr Leu Glu Asn Leu Leu
            260                 265                 270

Thr Trp Gln Ala Arg Gln Arg Thr Arg Arg His Leu His Asp Asn Val
        275                 280                 285

Gln Leu Ile Thr Gly Val Asp Phe Thr Gly Thr Thr Val Gly Phe Ala
    290                 295                 300
```

-continued

```
Arg Val Ser Ala Met Cys Ser His Ser Ser Gly Ala Val Asn Gln Asp
305                 310                 315                 320

His Ser Lys Asn Pro Val Gly Val Ala Ala Pro Trp Pro Met Arg Trp
                325                 330                 335

Ala Thr Thr Trp Ala Trp Thr Met Met Arg Thr Ser Arg Ala Ala Ala
                340                 345                 350

Ala Arg Asn Ala Ser Arg Pro Ala Ala Ala Ser Trp Gln Ala Ala Leu
            355                 360                 365

Ala Pro Val Ser Pro Gly Cys Ser Val Thr Ala Ala Arg Pro Thr Trp
        370                 375                 380

Arg Ala Phe Trp Ser Gly Arg
385                 390

<210> SEQ ID NO 7
<211> LENGTH: 8
<212> TYPE: PRT
<213> ORGANISM: Artificial Sequence
<220> FEATURE:
<223> OTHER INFORMATION: The source of this sequence is Scott, et al.
      (1992) Proc. Natl. A cad. Sci. USA 89:658-662, which is cited in
      Abe, et. al., on page 15, lines 29-30, of the Specification.  The
      sequence is derived from "G4 glycinin."
<220> FEATURE:
<221> NAME/KEY: MISC_FEATURE
<222> LOCATION: (1)..(8)
<223> OTHER INFORMATION: The sequence may be a substrate for proteases
      or peptidases.

<400> SEQUENCE: 7

Glu Thr Arg Asn Gly Val Glu Glu
1               5
```

US 6,638,507 B1

MAMMALIAN PROTEASES; RELATED REAGENTS

This application is a divisional application of 08/706,216, filed Aug. 30, 1996, now U.S. Pat. No. 6,140,098.

FIELD OF THE INVENTION

The present invention contemplates compositions related to proteins from animals, e.g., mammals, which function as proteases. In particular, it provides nucleic acids which encode, antibodies to, and proteins which exhibit biological functions, e.g., capacity to degrade proteinaceous substrates.

BACKGROUND OF THE INVENTION

The proteases are a very broad group of enzymes which carry out an enzymatic function of hydrolysing a peptide bond. Within the group, there is a wide range of substrate specificities for the amino acids adjacent the cleavage sites. Proteases are typically categorized on the basis of their catalytic mechanisms, e.g., based upon studies of their active sites, or by the effects of pH. Four main categories of proteases are serine proteinases, sulfhydryl proteases, acid proteases, and metalloproteases. They may also be classified according to their cleavage sites, e.g., endoproteases, amino peptidases, or carboxy peptidases.

Proteases have traditionally held a large share of the industrial enzyme market. Proteases are used in many industrial processes, including in detergents and cleaning products, e.g., to degrade protein materials such as blood and stains, in leather production, e.g., to remove hair, in baking, e.g., to break down glutens, in flavorings, e.g., soy sauce, in meat tenderizing, e.g., to break down collagen, in gelatin or food supplement production, in the textile industry, in waste treatment, and in the photographic industry. See, e.g., Gusek (1991) *Inform* 1:14–18; Zamost, et al. (1996) *J. Industrial Microbiol.* 8:71–82; James and Simpson (1996) *CRC Critical Reviews in Food Science and Nutrition* 36:437–463; Teichgraeber, et al. (1993) *Trends in Food Science and Technology* 4:145–149; Tjwan, et al. (1993) *J. Dairy Research* 60:269–286; Haard (1992) *J. Aquatic Food Product Technology* 1:17–35; van Dijk (1995) *Laundry and Cleaning News* 21:32–33; Nolte, et al. (1996) *J. Textile Institute* 87:212–226; Chikkodi, et al. (1995) *Textile Res. J.* 65:564–569; and Shih (1993) *Poultry Science* 72:1617–1620.

While there are many uses for proteases, there is always the need for a more active protease under various specific conditions. There is a need for new proteinases of differing properties, specificities, and activities.

SUMMARY OF THE INVENTION

The present invention provides a composition of matter selected from an antibody binding site which specifically binds to a human APG04, FDH02, or D1B2 protein or significant fragment thereof; an expression vector encoding a human APG04, FDH02, or D1B2 protein or significant fragment thereof; a substantially pure protein which is specifically recognized by the antibody binding site; and a substantially pure APG04, FDH02, or D1B2 protein or peptide thereof, or a fusion protein comprising at least a 30 amino acid fragment of human APG04, FDH02, or D1B2 protein sequence.

In the antibody binding site embodiments, the antibody binding site may be: specifically immunoreactive with a mature protein selected from the group consisting of the polypeptides of SEQ ID NO: 2, 4, and 6; raised against a purified or recombinantly produced human APG04, FDH02, or D1B2 protein; in a monoclonal antibody, Fab, or F(ab)2; or in a detectably labeled antibody. In certain embodiments; the antibody binding site is detected in a biological sample by a method of: contacting a binding agent having an affinity for the human APG04, FDH02, or D1B2 protein with the biological sample; incubating the binding agent with the biological sample to form a binding agent:human APG04, FDH02, or D1B2 protein complex; and detecting the complex. In a preferred embodiment, the biological sample is from a human, and the binding agent is an antibody.

A kit embodiment is provided comprising a composition, described above, with either instructional material for the use and/or disposal of the composition and products; or segregation of the composition into a compartment or container.

A nucleic acid embodiment of the invention includes an expression vector encoding a human APG04, FDH02, or D1B2 protein, wherein the protein specifically binds an antibody generated against an immunogen selected from the mature polypeptide portions of SEQ ID NO: 2, 4, and 6. The vector may: encode a human APG04, FDH02, or D1B2 polypeptide with complete sequence identity to a naturally occurring human APG04, FDH02, or D1B2 protein; encode a human APG04, FDH02, or D1B2 protein comprising sequence selected from the polypeptides of SEQ ID NO: 2, 4, and 6; or comprise sequence selected from the nucleic acids of SEQ ID NO: 1, 3, or 5. In other embodiments, the vector is capable of selectively hybridizing to a nucleic acid encoding a natural human APG04, FDH02, or D1B2 protein, e.g., a mature protein coding segment of SEQ ID NO: 1, 3, or 5. In various preferred embodiments, the isolated nucleic acid is detected in a biological sample by a method: contacting a biological sample with a nucleic acid probe capable of selectively hybridizing to the nucleic acid; incubating the nucleic acid probe with the biological sample to form a hybrid of the nucleic acid probe with complementary nucleic acid sequences present in the biological sample; and determining the extent of hybridization of the nucleic acid probe to the complementary nucleic acid sequences. In such method, preferably the nucleic acid probe is capable of hybridizing to a nucleic acid encoding a protein consisting of the polypeptides of SEQ ID NO: 2, 4, or 6.

In protein embodiments, the human APG04, FDH02, or D1B2 protein specifically binds to an antibody generated against the respective immunogen; e.g., the polypeptides of SEQ ID NO: 2, 4, or 6. In various embodiments, the isolated human APG04, FDH02, or D1B2 protein consists of a polypeptide comprising sequence from SEQ ID NO: 2, 4, or 6; is recombinantly produced, or is a naturally occurring protein.

The present invention also embraces a cell transfected with the isolated or recombinant nucleic acid encoding a human APG04, FDH02, or D1B2 protein, e.g., where the nucleic acid has SEQ ID NO: 1, 3, or 5.

DETAILED DESCRIPTION

OUTLINE

I. General

II. Definitions

III. Nucleic Acids

IV. Making APG04, FDH02, or D1B2 Protein

V. Antibodies a. antibody production
b. immunoassays
VI. Purified APG04, FDH02, and D1B2 Protein
VII. Physical Variants
VIII. Binding Agent: APG04, FDH02, and D1B2 Protein Complexes
IX. Functional Variants
X. Uses
XI. Kits
XII. Substrate Identification
I. General The present invention provides DNA sequences encoding mammalian proteins which exhibit structural properties or motifs characteristic of a protease. The proteases described herein are designated APG04, FDH02 and D1B2. See Tables 1, 2, and 3.

The descriptions below are directed, for exemplary purposes, to primate embodiments, e.g., human, but are likewise applicable to related embodiments from other, e.g., natural, sources. These sources should, where appropriate, include various vertebrates, typically warm blooded animals, e.g., birds and mammals, particularly domestic animals, and primates.

TABLE 1

Human APG04 nucleotide and predicted amino acid sequence. SEQ ID NO: 1 and 2. The predicted leader sequence is underlined. The mature peptide probably begins about at Pro (position 21). Active site/zinc chelating residues are indicated by *.

```
TTGATGGCCA CCAGGTGATC TCTGGTCTCT TCAGTGTGGC TTTGCAGACT ATAAAGGCGC     60

AGCGCGCCAA CGAGGCGGGT TGGCCCCAGA CGGCGGAGAG GAAGGGCAGA GTCGGCGGTC    120

CTGAGACTTG GGGCGGCCCC TTGGAGGTCA GCCCCGCTCG CTCCTCCCGG CCCTCTCCTC    180

CTCTCCGAGG TCCGAGGCGG GCAGCGGGCT GTGGGCGGGC AGGAGGCTGC GGAGGGGCGG    240

GGGGCAGGAA GGGGCGGGGG GCTCGGCGCA CTCGGCAGGA AGAGACCGAC CCGCCACCCG    300

CCGTAGCCCG CGCGCCCCTG GCACTCAATC CCCGCC ATG TGG GGG CTC CTG CTC     354
                                         Met Trp Gly Leu Leu Leu
                                          1               5

GCC CTG GCC GCC TTC GCG CCG GCC GTC GGC CCG GCT CTG GGG GCG CCC     402
Ala Leu Ala Ala Phe Ala Pro Ala Val Gly Pro Ala Leu Gly Ala Pro
             10                  15                  20

AGG AAC TCG GTG CTG GGC CTC GCG CAG CCC GGG ACC ACC AAG GTC CCA     450
Arg Asn Ser Val Leu Gly Leu Ala Gln Pro Gly Thr Thr Lys Val Pro
         25                  30                  35

GGC TCG ACC CCG GCC CTG CAT AGC AGC CCG GCA CAG CCG CCG GCG GAG     498
Gly Ser Thr Pro Ala Leu His Ser Ser Pro Ala Gln Pro Pro Ala Glu
     40                  45                  50

ACA GCT AAC GGG ACC TCA GAA CAG CAT GTC CGG ATT CGA GTC ATC AAG     546
Thr Ala Asn Gly Thr Ser Glu Gln His Val Arg Ile Arg Val Ile Lys
 55                  60                  65                  70

AAG AAA AAG GTC ATT ATG AAG AAG CGG AAG AAG CTA ACT CTA ACT CGC     594
Lys Lys Lys Val Ile Met Lys Lys Arg Lys Lys Leu Thr Leu Thr Arg
                 75                  80                  85

CCC ACC CCA CTG GTG ACT GCC GGG CCC CTT GTG ACC CCC ACT CCA GCA     642
Pro Thr Pro Leu Val Thr Ala Gly Pro Leu Val Thr Pro Thr Pro Ala
             90                  95                 100

GGG ACC CTC GAC CCC GCT GAG AAA CAA GAA ACA GGC TGT CCT CCT TTG     690
Gly Thr Leu Asp Pro Ala Glu Lys Gln Glu Thr Gly Cys Pro Pro Leu
         105                 110                 115

GGT CTG GAG TCC CTG CGA GTT TCA GAT AGC CGG CTT GAG GCA TCC AGC     738
Gly Leu Glu Ser Leu Arg Val Ser Asp Ser Arg Leu Glu Ala Ser Ser
     120                 125                 130

AGC CAG TCC TTT GGT CTT GGA CCA CAC CGA GGA CGG CTC AAC ATT CAG     786
Ser Gln Ser Phe Gly Leu Gly Pro His Arg Gly Arg Leu Asn Ile Gln
135                 140                 145                 150

TCA GGC CTG GAG GAC GGC GAT CTA TAT GAT GGA GCC TGG TGT GCT GAG     834
Ser Gly Leu Glu Asp Gly Asp Leu Tyr Asp Gly Ala Trp Cys Ala Glu
                 155                 160                 165

GAG CAG GAC GCC GAT CCA TGG TTT CAG GTG GAC GCT GGG CAC CCC ACC     882
Glu Gln Asp Ala Asp Pro Trp Phe Gln Val Asp Ala Gly His Pro Thr
             170                 175                 180
```

TABLE 1-continued

Human APG04 nucleotide and predicted amino acid sequence. SEQ ID
NO: 1 and 2. The predicted leader sequence is underlined. The mature
peptide probably begins about at Pro (position 21). Active site/zinc
chelating residues are indicated by *.

```
CGC TTC TCG GGT GTT ATC ACA CAG GGC AGG AAC TCT GTC TGG AGG TAT       930
Arg Phe Ser Gly Val Ile Thr Gln Gly Arg Asn Ser Val Trp Arg Tyr
        185                 190                 195

GAC TGG GTC ACA TCA TAC AAG GTC CAG TTC AGC AAT GAC AGT CGG ACC       978
Asp Trp Val Thr Ser Tyr Lys Val Gln Phe Ser Asn Asp Ser Arg Thr
    200                 205                 210

TGG TGG GGA AGT AGG AAC CAC AGC AGT GGG ATG GAC GCA GTA TTT CCT      1026
Trp Trp Gly Ser Arg Asn His Ser Ser Gly Met Asp Ala Val Phe Pro
215                 220                 225                 230

GCC AAT TCA GAC CCA GAA ACT CCA GTG CTG AAC CTC CTG CCG GAG CCC      1074
Ala Asn Ser Asp Pro Glu Thr Pro Val Leu Asn Leu Leu Pro Glu Pro
                235                 240                 245

CAG GTG GCC CGC TTC ATT CGC CTG CTG CCC CAG ACC TGG CTC CAG GGA      1122
Gln Val Ala Arg Phe Ile Arg Leu Leu Pro Gln Thr Trp Leu Gln Gly
            250                 255                 260

GGC GCG CCT TGC CTC CGG GCA GAG ATC CTG GCC TGC CCA GTC TCA GAC      1170
Gly Ala Pro Cys Leu Arg Ala Glu Ile Leu Ala Cys Pro Val Ser Asp
            265                 270                 275

CCC AAT GAC CTA TTC CTT GAG GCC CCT GCG TCG GGA TCC TCT GAC CCT      1218
Pro Asn Asp Leu Phe Leu Glu Ala Pro Ala Ser Gly Ser Ser Asp Pro
        280                 285                 290

CTA GAC TTT CAG CAT CAC AAT TAC AAG GCC ATG AGG AAG CTG ATG AAG      1266
Leu Asp Phe Gln His His Asn Tyr Lys Ala Met Arg Lys Leu Met Lys
295                 300                 305                 310

CAG GTA CAA GAG CAA TGC CCC AAC ATC ACC CGC ATC TAC AGC ATT GGG      1314
Gln Val Gln Glu Gln Cys Pro Asn Ile Thr Arg Ile Tyr Ser Ile Gly
                315                 320                 325

AAG AGC TAC CAG GGC CTG AAG CTG TAT GTG ATG GAA ATG TCG GAC AAG      1362
Lys Ser Tyr Gln Gly Leu Lys Leu Tyr Val Met Glu Met Ser Asp Lys
            330                 335                 340

CCT GGG GAG CAT GAG CTG GGG GAG CCT GAG GTG CGC TAC GTG GCT GGC      1410
Pro Gly Glu His Glu Leu Gly Glu Pro Glu Val Arg Tyr Val Ala Gly
        345                 350                 355

ATG CAT GGG AAC GAG GCC CTG GGG CGG GAG TTG CTT CTG CTC CTG ATG      1458
Met His Gly Asn Glu Ala Leu Gly Arg Glu Leu Leu Leu Leu Leu Met
     *         *
    360                 365                 370

CAG TTC CTG TGC CAT GAG TTC CTG CGA GGG AAC CCA CAG GTG ACC CGG      1506
Gln Phe Leu Cys His Glu Phe Leu Arg Gly Asn Pro Gln Val Thr Arg
                                         *
375                 380                 385                 390

CTG CTC TCT GAG ATG CGC ATT CAC CTG CTG CCC TCC ATG AAC CCT GAT      1554
Leu Leu Ser Glu Met Arg Ile His Leu Leu Pro Ser Met Asn Pro Asp
                395                 400                 405

GGC TAT GAG ATC GCC TAC CAC CGG GGT TCA GAG CTG GTG GGC TGG GCC      1602
Gly Tyr Glu Ile Ala Tyr His Arg Gly Ser Glu Leu Val Gly Trp Ala
            410                 415                 420

GAG GGC CGC TGG AAC AAC CAG AGC ATC GAT CTT AAC CAT AAT TTT GCT      1650
Glu Gly Arg Trp Asn Asn Gln Ser Ile Asp Leu Asn His Asn Phe Ala
        425                 430                 435

GAC CTC AAC ACA CCA CTG TGG GAA GCA CAG GAC GAT GGG AAG GTG CCC      1698
Asp Leu Asn Thr Pro Leu Trp Glu Ala Gln Asp Asp Gly Lys Val Pro
    440                 445                 450

CAC ATC GTC CCC AAC CAT CAC CTG CCA TTG CCC ACT TAC TAC ACC CTG      1746
His Ile Val Pro Asn His His Leu Pro Leu Pro Thr Tyr Tyr Thr Leu
455                 460                 465                 470
```

TABLE 1-continued

Human APG04 nucleotide and predicted amino acid sequence. SEQ ID NO: 1 and 2. The predicted leader sequence is underlined. The mature peptide probably begins about at Pro (position 21). Active site/zinc chelating residues are indicated by •.

| | |
|---|---|
| CCC AAT GCC ACC GTG GCT CCT GAA ACG CGG GCA GTA ATC AAG TGG ATG<br>Pro Asn Ala Thr Val Ala Pro Glu Thr Arg Ala Val Ile Lys Trp Met<br>                     475                 480                 485 | 1794 |
| AAG CGG ATC CCC TTT GTG CTA AGT GCC AAC CTC CAC GGG GGT GAG CTC<br>Lys Arg Ile Pro Phe Val Leu Ser Ala Asn Leu His Gly Gly Glu Leu<br>                 490                 495          •      500 | 1842 |
| GTG GTG TCC TAC CCA TTC GAC ATG ACT CGC ACC CCG TGG GCT GCC CGC<br>Val Val Ser Tyr Pro Phe Asp Met Thr Arg Thr Pro Trp Ala Ala Arg<br>             505                 510                 515 | 1890 |
| GAG CTC ACG CCC ACA CCA GAT GAT GCT GTG TTT CGC TGG CTC AGC ACT<br>Glu Leu Thr Pro Thr Pro Asp Asp Ala Val Phe Arg Trp Leu Ser Thr<br>         520                 525                 530 | 1938 |
| GTC TAT GCT GGC AGT AAT CTG GCC ATG CAG GAC ACC AGC CGC CGA CCC<br>Val Tyr Ala Gly Ser Asn Leu Ala Met Gln Asp Thr Ser Arg Arg Pro<br>535                 540                 545                 550 | 1986 |
| TGC CAC AGC CAG GAC TTC TCC GTG CAC GGC AAC ATC ATC AAC GGG GCT<br>Cys His Ser Gln Asp Phe Ser Val His Gly Asn Ile Ile Asn Gly Ala<br>             555                 560                 565 | 2034 |
| GAC TGG CAC ACG GTC CCC GGG AGC ATG AAT GAC TTC AGC TAC CTA CAC<br>Asp Trp His Thr Val Pro Gly Ser Met Asn Asp Phe Ser Tyr Leu His<br>             570                 575                 580 | 2082 |
| ACC AAC TGC TTT GAG GTC ACT GTG GAG CTG TCC TGT GAC AAG TTC CCT<br>Thr Asn Cys Phe Glu Val Thr Val Glu Leu Ser Cys Asp Lys Phe Pro<br>             585                 590                 595 | 2130 |
| CAC GAG AAT GAA TTG CCC CAG GAG TGG GAG AAC AAC AAA GAC GCC CTC<br>His Glu Asn Glu Leu Pro Gln Glu Trp Glu Asn Asn Lys Asp Ala Leu<br>         600                 605                 610 | 2178 |
| CTC ACC TAC CTG GAG CAG GTG CGC ATG GGC ATT GCA GGA GTG GTG AGG<br>Leu Thr Tyr Leu Glu Gln Val Arg Met Gly Ile Ala Gly Val Val Arg<br>615                 620                 625                 630 | 2226 |
| GAC AAG GAC ACG GAG CTT GGG ATT GCT GAC GCT GTC ATT GCC GTG GAT<br>Asp Lys Asp Thr Glu Leu Gly Ile Ala Asp Ala Val Ile Ala Val Asp<br>                 635                 640                 645 | 2274 |
| GGG ATT AAC CAT GAC GTG ACC ACG GCG TGG GGC GGG GAT TAT TGG CGT<br>Gly Ile Asn His Asp Val Thr Thr Ala Trp Gly Gly Asp Tyr Trp Arg<br>             650                 655                 660 | 2322 |
| CTG CTG ACC CCA GGG GAC TAC ATG GTG ACT GCC AGT GCC GAG GGC TAC<br>Leu Leu Thr Pro Gly Asp Tyr Met Val Thr Ala Ser Ala Glu Gly Tyr<br>             665                 670                 675 | 2370 |
| CAT TCA GTG ACA CGG AAC TGT CGG GTC ACC TTT GAA GAG GGC CCC TTC<br>His Ser Val Thr Arg Asn Cys Arg Val Thr Phe Glu Glu Gly Pro Phe<br>         680                 685                 690 | 2418 |
| CCC TGC AAT TTC GTG CTC ACC AAG ACT CCC AAA CAG AGG CTG CGC GAG<br>Pro Cys Asn Phe Val Leu Thr Lys Thr Pro Lys Gln Arg Leu Arg Glu<br>695                 700                 705                 710 | 2466 |
| CTG CTG GCA GCT GGG GCC AAG GTG CCC CCG GAC CTT CGC AGG CGC CTG<br>Leu Leu Ala Ala Gly Ala Lys Val Pro Pro Asp Leu Arg Arg Arg Leu<br>                 715                 720                 725 | 2514 |
| GAG CGG CTA AGG GGA CAG AAG GAT TGA TACCTGCGGT TTAAGAGCCC<br>Glu Arg Leu Arg Gly Gln Lys Asp  *<br>             730                 735 | 2561 |

TABLE 1-continued

Human APG04 nucleotide and predicted amino acid sequence. SEQ ID NO: 1 and 2. The predicted leader sequence is underlined. The mature peptide probably begins about at Pro (position 21). Active site/zinc chelating residues are indicated by •.

```
TAGGGCAGGC TGGACCTGTC AAGACGGGAA GGGGAAGAGT AGAGAGGGAG GGACAAAGTG    2621

AGGAAAAGGT GCTCATTAAA GCTACCGGGC ACCTTAAAAA AAAAAAAAAA AAAAAAAAA     2681

AAAAAAAAAA AAAAAAAAAA AAAAAAGGG CGGCCGCT                             2719
```

TABLE 2

Human FDH02 nucleotide and predicted amino acid sequence. SEQ ID NO: 3 and 4. The predicted signal sequence is underlined. The mature peptide should begin about at Asp (position 21).

```
CAGGTACCGG TCCGGAATTC CCGGGTCGAC CCACGCGTCC GGTTTGGTGT GAGGCTGCGA    60

GCCGCCGCGA GTTCTCACGG TCCCGCCGGC GCCACCACCG CGGTCACTCA CCGCCGCCGC   120

CGCCACCACT GCCACCACGG TCGCCTGCCA CAGGTGTCTG CAATTGAACT CCAAGGTGCA   180

GA ATG GTT TGG AAA GTA GCT GTA TTC CTC AGT GTG GCC CTG GGC ATT      227
   Met Val Trp Lys Val Ala Val Phe Leu Ser Val Ala Leu Gly Ile
   1               5                   10                  15

GGT GCC GTT CCT ATA GAT GAT CCT GAA GAT GGA GGC AAG CAC TGG GTG     275
Gly Ala Val Pro Ile Asp Asp Pro Glu Asp Gly Gly Lys His Trp Val
                20                  25                  30

GTG ATC GTG GCA GGT TCA AAT GGC TGG TAT AAT TAT AGG CAC CAG GCA     323
Val Ile Val Ala Gly Ser Asn Gly Trp Tyr Asn Tyr Arg His Gln Ala
                35                  40                  45

GAC GCG TGC CAT GCC TAC CAG ATC ATT CAC CGC AAT GGG ATT CCT GAC     371
Asp Ala Cys His Ala Tyr Gln Ile Ile His Arg Asn Gly Ile Pro Asp
            50                  55                  60

GAA CAG ATC GTT GTG ATG ATG TAC GAT GAC ATT GCT TAC TCT GAA GAC     419
Glu Gln Ile Val Val Met Met Tyr Asp Asp Ile Ala Tyr Ser Glu Asp
        65                  70                  75

AAT CCC ACT CCA GGA ATT GTG ATC AAC AGG CCC AAT GGC ACA GAT GTC     467
Asn Pro Thr Pro Gly Ile Val Ile Asn Arg Pro Asn Gly Thr Asp Val
80                  85                  90                  95

TAT CAG GGA GTC CCG AAG GAC TAC ACT GGA GAG GAT GTT ACC CCA CAA     515
Tyr Gln Gly Val Pro Lys Asp Tyr Thr Gly Glu Asp Val Thr Pro Gln
                100                 105                 110

AAT TTC CTT GCT GTG TTG AGA GGC GAT GCA GAA GCA GTG AAG GGC ATA     563
Asn Phe Leu Ala Val Leu Arg Gly Asp Ala Glu Ala Val Lys Gly Ile
                115                 120                 125

GGA TCC GGC AAA GTC CTG AAG AGT GGC CCC CAG GAT CAC GTG TTC ATT     611
Gly Ser Gly Lys Val Leu Lys Ser Gly Pro Gln Asp His Val Phe Ile
                130                 135                 140

TAC TTC ACT GAC CAT GGA TCT ACT GGA ATA CTG GTT TTT CCC AAT GAA     659
Tyr Phe Thr Asp His Gly Ser Thr Gly Ile Leu Val Phe Pro Asn Glu
            145                 150                 155

GAT CTT CAT GTA AAG GAC CTG AAT GAG ACC ATC CAT TAC ATG TAC AAA     707
Asp Leu His Val Lys Asp Leu Asn Glu Thr Ile His Tyr Met Tyr Lys
160                 165                 170                 175

CAC AAA ATG TAC CGA AAG ATG GTG TTC TAC ATT GAA GCC TGT GAG TCT     755
His Lys Met Tyr Arg Lys Met Val Phe Tyr Ile Glu Ala Cys Glu Ser
                180                 185                 190

GGG TCC ATG ATG AAC CAC CTG CCG GAT AAC ATC AAT GTT TAT GCA ACT     803
Gly Ser Met Met Asn His Leu Pro Asp Asn Ile Asn Val Tyr Ala Thr
                195                 200                 205
```

TABLE 2-continued

Human FDH02 nucleotide and predicted amino acid sequence. SEQ ID
NO: 3 and 4. The predicted signal sequence is underlined. The mature
peptide should begin about at Asp (position 21).

| | |
|---|---|
| ACT GCT GCC AAC CCC AGA GAG TCG TCC TAC GCC TGT TAC TAT GAT GAG<br>Thr Ala Ala Asn Pro Arg Glu Ser Ser Tyr Ala Cys Tyr Tyr Asp Glu<br>        210                  215                  220 | 851 |
| AAG AGG TCC ACG TAC CTG GGG GAC TGG TAC AGC GTC AAC TGG ATG GAA<br>Lys Arg Ser Thr Tyr Leu Gly Asp Trp Tyr Ser Val Asn Trp Met Glu<br>    225                  230                  235 | 899 |
| GAC TCG GAC GTG GAA GAT CTG ACT AAA GAG ACC CTG CAC AAG CAG TAC<br>Asp Ser Asp Val Glu Asp Leu Thr Lys Glu Thr Leu His Lys Gln Tyr<br>240                  245                  250                  255 | 947 |
| CAC CTG GTA AAA TCG CAC ACC AAC ACC AGC CAC GTC ATG CAG TAT GGA<br>His Leu Val Lys Ser His Thr Asn Thr Ser His Val Met Gln Tyr Gly<br>            260                  265                  270 | 995 |
| AAC AAA ACA ATC TCC ACC ATG AAA GTG ATG CAG TTT CAG GGT ATG AAA<br>Asn Lys Thr Ile Ser Thr Met Lys Val Met Gln Phe Gln Gly Met Lys<br>            275                  280                  285 | 1043 |
| CGC AAA GCC AGT TCT CCC GTC CCC CTA CCT CCA GTC ACA CAC CTT GAC<br>Arg Lys Ala Ser Ser Pro Val Pro Leu Pro Pro Val Thr His Leu Asp<br>    290                  295                  300 | 1091 |
| CTC ACC CCC AGC CCT GAT GTG CCT CTC ACC ATC ATG AAA AGG AAA CTG<br>Leu Thr Pro Ser Pro Asp Val Pro Leu Thr Ile Met Lys Arg Lys Leu<br>305                  310                  315 | 1139 |
| ATG AAC ACC AAT GAT CTG GAG GAG TCC AGG CAG CTC ACG GAG GAG ATC<br>Met Asn Thr Asn Asp Leu Glu Glu Ser Arg Gln Leu Thr Glu Glu Ile<br>320                  325                  330                  335 | 1187 |
| CAG CGG CAT CTG GAT GCC AGG CAC CTC ATT GAG AAG TCA GTG CGT AAG<br>Gln Arg His Leu Asp Ala Arg His Leu Ile Glu Lys Ser Val Arg Lys<br>            340                  345                  350 | 1235 |
| ATC GTC TCC TTG CTG GCA GCG TCC GAG GCT GAG GTG GAG CAG CTC CTG<br>Ile Val Ser Leu Leu Ala Ala Ser Glu Ala Glu Val Glu Gln Leu Leu<br>            355                  360                  365 | 1283 |
| TCC GAG AGA GCC CCG CTC ACG GGG CAC AGC TGC TAC CCA GAG GCC CTG<br>Ser Glu Arg Ala Pro Leu Thr Gly His Ser Cys Tyr Pro Glu Ala Leu<br>    370                  375                  380 | 1331 |
| CTG CAC TTC CGG ACC CAC TGC TTC AAC TGG CAC TCC CCC ACG TAC GAG<br>Leu His Phe Arg Thr His Cys Phe Asn Trp His Ser Pro Thr Tyr Glu<br>385                  390                  395 | 1379 |
| TAT GCG TTG AGA CAT TTG TAC GTG CTG GTC AAC CTT TGT GAG AAG CCG<br>Tyr Ala Leu Arg His Leu Tyr Val Leu Val Asn Leu Cys Glu Lys Pro<br>400                  405                  410                  415 | 1427 |
| TAT CCA CTT CAC AGG ATA AAA TTG TCC ATG GAC CAC GTG TGC CTT GGT<br>Tyr Pro Leu His Arg Ile Lys Leu Ser Met Asp His Val Cys Leu Gly<br>            420                  425                  430 | 1475 |
| CAC TAC TGA AGAGCTGCCT CCTGGAAGCT TTTCCAAGTG TGAGCGCCCC<br>His Tyr  * | 1524 |
| CCCGACTGTG TGCTGATCAG AGACTGGAGA GGTGGAGTGA GAAGTCTCCG CTGCTCGGGC | 1584 |
| CCTCCTGGGG AGCCCCCGCT CCAGGGCTCG CTCCAGGACC TTCTTCACAA GATGACTTGC | 1644 |
| TCGCTGTTAC CTGCTTCCCC AGTCTTTTCT GAAAAACTAC AAATTAGGGT GGGAAAAGCT | 1704 |
| CTGTATTGAG AAGGGTCATA TTTGCTTTCT AGGAGGTTTG TTGTTTTGCC TGTTAGTTTT | 1764 |
| GAGGAGCAGG AAGCTCATGG GGGCTTCTGT AGCCCCTCTC AAAAGGAGTC TTTATTCTGA | 1824 |
| GAATTTGAAG CTGAAACCTC TTTAAATTTT CAGAATGATT TTATTGAAGA GGGCCGCAAG | 1884 |
| CCCCAAATGG AAAACTGTTT TTAGAAAATA TGATGATTTT TGATTGCTTT TGTATTTAAT | 1944 |

TABLE 2-continued

Human FDH02 nucleotide and predicted amino acid sequence. SEQ ID NO: 3 and 4. The predicted signal sequence is underlined. The mature peptide should begin about at Asp (position 21).

| | |
|---|---:|
| TCTGCAGGTG TTCAAGTCTT AAAAAATAAA GATTTATAAC AGAACCCAAA AAAAAAAAAA | 2004 |
| AAAAAAAAAA AAAAAAGGGC GGCCGC | 2030 |

TABLE 3

Human D1B2 (MS2) partial nucleic acid and predicted amino acid sequence. SEQ ID NO: 5 and 6. The predicted signal sequence is underlined. The mature peptide should begin about at Ser (position 20).

```
ATG CGC GGT CTC GGG CTC TGG CTG CTG GGC GCG ATG ATG CTG CCT GCG      48
Met Arg Gly Leu Gly Leu Trp Leu Leu Gly Ala Met Met Leu Pro Ala
 1               5                  10                  15

ATT GCC CCC AGC CGG CCC TGG GCC CTC ATG GAG CAG TAT GAG GTC GTG      96
Ile Ala Pro Ser Arg Pro Trp Ala Leu Met Glu Gln Tyr Glu Val Val
                20                  25                  30

TTG CCG CGG TGT CTG CCA GGC CCC CGA GTC CGC CGA GCT CTG CCC TCC     144
Leu Pro Arg Cys Leu Pro Gly Pro Arg Val Arg Arg Ala Leu Pro Ser
            35                  40                  45

CAC TTG GGC CTG CAC CCA GAG AGG GTG AGC TAC GTC CTT GGG GCC ACA     192
His Leu Gly Leu His Pro Glu Arg Val Ser Tyr Val Leu Gly Ala Thr
     50                  55                  60

GGG CAC AAC TTC ACC CTC CAC CTG CGG AAG AAC AGG GAC CTG CTG GGT     240
Gly His Asn Phe Thr Leu His Leu Arg Lys Asn Arg Asp Leu Leu Gly
 65                  70                  75                  80

TCC GGC TAC ACA GAG ACC TAT ACG GCT GCC AAT GGC TCC GAG GTG ACG     288
Ser Gly Tyr Thr Glu Thr Tyr Thr Ala Ala Asn Gly Ser Glu Val Thr
                85                  90                  95

GAG CAG CCT CGC GGG CAG GAC CAC TGC TTC TAC CAG GGC CAC GTA GAG     336
Glu Gln Pro Arg Gly Gln Asp His Cys Phe Tyr Gln Gly His Val Glu
                100                 105                 110

GGG TAC CCG GAC TCA GCC GCC AGC CTC AGC ACC TGT GCC GGC CTC AGG     384
Gly Tyr Pro Asp Ser Ala Ala Ser Leu Ser Thr Cys Ala Gly Leu Arg
            115                 120                 125

GGT TTC TTC CAG GTG GGG TCA GAC CTG CAC CTG ATC GAG CCC CTG GAT     432
Gly Phe Phe Gln Val Gly Ser Asp Leu His Leu Ile Glu Pro Leu Asp
        130                 135                 140

GAA GGT GGC GAG GGC GGA CGG CAC GCC GTG TAC CAG GCT GAG CAC CTG     480
Glu Gly Gly Glu Gly Gly Arg His Ala Val Tyr Gln Ala Glu His Leu
145                 150                 155                 160

CTG CAG ACG GCC GGG ACC TGC GGG GTC AGC GAC GAC AGC CTG GGC AGC     528
Leu Gln Thr Ala Gly Thr Cys Gly Val Ser Asp Asp Ser Leu Gly Ser
                165                 170                 175

CTC CTG GGA CCC CGG ACG GCA GCC GTC TTC AGG CCT CGG CCC GGG GAC     576
Leu Leu Gly Pro Arg Thr Ala Ala Val Phe Arg Pro Arg Pro Gly Asp
            180                 185                 190

TCT CTG CCA TCC CGA GAG ACC CGC TAC GTG GAG CTG TAT GTG GTC GTG     624
Ser Leu Pro Ser Arg Glu Thr Arg Tyr Val Glu Leu Tyr Val Val Val
        195                 200                 205

GAC AAT GCA GAG TTC CAG ATG CTG GGG AGC GAA GCA GCC GTG CGT CAT     672
Asp Asn Ala Glu Phe Gln Met Leu Gly Ser Glu Ala Ala Val Arg His
        210                 215                 220

CGG GTG CTG GAG GTG GTG AAT CAC GTG GAC AAG CTA TAT CAG AAA CTC     720
Arg Val Leu Glu Val Val Asn His Val Asp Lys Leu Tyr Gln Lys Leu
225                 230                 235                 240

AAC TTC CGT GTG GTC CTG GTG GGC CTG GAG ATT TGG AAT AGT CAG GAC     768
```

TABLE 3-continued

Human D1B2 (MS2) partial nucleic acid and predicted amino acid sequence. SEQ ID NO: 5 and 6. The predicted signal sequence is underlined. The mature peptide should begin about at Ser (position 20).

```
Asn Phe Arg Val Val Leu Val Gly Leu Glu Ile Trp Asn Ser Gln Asp
            245             250                 255

AGG TTC CAC GTC AGC CCC GAC CCC AGT GTC ACA CTG GAG AAC CTC CTG    816
Arg Phe His Val Ser Pro Asp Pro Ser Val Thr Leu Glu Asn Leu Leu
            260             265                 270

ACC TTG CAG GCA CGG CAA CGG ACA CGG CGG CAC CTG CAT GAC AAC GTA    864
Thr Trp Gln Ala Arg Gln Arg Thr Arg Arg His Leu His Asp Asn Val
            275             280                 285

CAG CTC ATC ACG GGT GTC GAC TTC ACC GGG ACT ACT GTG GGG TTT GCC    912
Gln Leu Ile Thr Gly Val Asp Phe Thr Gly Thr Thr Val Gly Phe Ala
            290             295                 300

AGG GTG TCC GCC ATG TGC TCC CAC AGC TCA GGG GCT GTG AAC CAG GAC    960
Arg Val Ser Ala Met Cys Ser His Ser Ser Gly Ala Val Asn Gln Asp
305             310             315                 320

CAC AGC AAG AAC CCC GTG GGC GTG GCT GCA CCA TGG CCC ATG AGA TGG    1008
His Ser Lys Asn Pro Val Gly Val Ala Ala Pro Trp Pro Met Arg Trp
            325             330                 335

GCC ACA ACC TGG GCA TGG ACC ATG ATG AGA ACG TCC AGG GCT GCC GCT    1056
Ala Thr Thr Trp Ala Trp Thr Met Met Arg Thr Ser Arg Ala Ala Ala
            340             345                 350

GCC AGG AAC GCT TCG AGG CCG GCC GCT GCA TCA TGG CAG GCA GCA TTG    1104
Ala Arg Asn Ala Ser Arg Pro Ala Ala Ala Ser Trp Gln Ala Ala Leu
            355             360                 365

GCT CCA GTT TCC CCA GGA TGT TCA GTG ACT GCA GCC AGG CCT ACC TGG    1152
Ala Pro Val Ser Pro Gly Cys Ser Val Thr Ala Ala Arg Pro Thr Trp
            370             375                 380

AGA GCT TTT TGG AGC GGC CGC                                        1173
Arg Ala Phe Trp Ser Gly Arg
385             390
```

The proteases of this invention are defined in part by their sequences, and by their physicochemical and biological properties. The biological properties of the human proteases described herein, e.g., human APG04, D1B2, and GFD02, are defined by their amino acid sequences, and mature sizes. They also should share certain biological enzymatic properties.

The human protease APG04 is a carboxypeptidase H domain containing protein isolated from CD1a+ CD34+ dendritic cells. This protein family includes soluble enzymes which process hormones from precursors. APG04 shares amino acid homology to aebp1, a soluble transcriptional repressor, a bone-related carboxypeptidase 2', and other carboxypeptidases which cleave at aa-lys and aa-arg peptidyl bonds. See, e.g., Manser, et al. (1990) Biochem. J. 267:517–525; He, et al. (1995) Nature 378:92–96; and Jung, et al. (1991) Mol. Endocrinol. 5:1257–1268. Known physiological substrates for this family of carboxypeptidases include, e.g., enkephalin and bradykinin. APG04 does not appear to contain a transmembrane domain. Expression analysis found this protease to be a late activation marker in dendritic cells. Other homologs from GenBank include X80478, S80565, U01909, X14329, X04411, aebp1, bone 2, P12259C1, P00451C1, P00451C2, and P21056. Signal was also detected in U937 monocytic cells and B cells, suggesting a physiological role in immuno function.

FHD02, also isolated from dendritic cells, exhibits amino acid homology to several hemaglobinases of some parasites and proteases from various seeds or fruits. See, e.g., Klinkert, et al. (1989) Mol. Biochem. Parasitol. 33:113–122; el Meanawy, et al. (1990) Am. J. Trop. Med. Hyg. 43:67–78; Davis, et al. (1987) J. Biol. Chem. 262:12851–12858; and Becker, et al. (1995) Eur. J. Biochem. 228:456–462. Substrates for a related protease, asparaginyl endopeptidase, are described in Abe, et al. (1993) J. Biol. Chem. 268:3525–3429, which also are prime candidates of substrates for FDH02. FHD02 shares significant nucleic acid homology with an EST of unidentified function, from GenBank, designated emb|OF1300|HSBC6B022. In addition to dendritic cells, FHD02 is expressed in placenta, spleen, small intestine, and monocytes treated with LPS and IFN-γ.

D1B2 is the human homolog of a mouse antigen designated mouse MS2. The extracellular region contains a clear metalloproteinase domain related to a family of several well characterized snake venom proteins which seem to inhibit blood clotting processes, e.g., Jararhagin precursor. See, e.g., Gomis-Rueth, et al. (1994) J. Mol. Biol. 239:513–544; Yoshida, et al. (1990) Int'l. Immunol. 2:585–591; Takeya, et al. (1989) J. Biochem 106:151–157; and de Araujo, et al. (1995) Arch. Biochem. Biophys. 320:141–148. The similarity in sequence comparison with the snake venom proteins extends beyond the protease activity domain, implying a second functional domain in the protein, called the disintegin domain, a platelet aggregation inhibitor. See, e.g., Katagiri, et al. (1995) Cytogenet. Cell Genet. 68:39–44; and Emi, et al. (1993) Nat. Genet. 5:151–157. Based on the strong structural homology with these snake venom proteins, likely substrates for D1B2 may include, e.g., insulin, type IV collagen, or fibrinogen.

D1B2 was initially found by subtraction of a resting dendritic cell library and a monocyte library. The full length clone was isolated from a 70% CD1a+ library (CD34+ hematopoietic progenitor cells cultured for 12 days in GM-CSF and TNFα). D1B2 shares approximately 68% identity with mouse MS2. Mouse MS2 is expressed mainly in macrophages, whereas D1B2 is expressed mainly in monocytes, resting and activated dendritic cells, resting Th1 cells, activated T cells, activated PBLs, and activated spleen cells.

One of skill will readily recognize that some sequence variations may be tolerated, e.g., conservative substitutions or positions remote from the critical helical structures and remote from the identified critical active site regions, without altering significantly the biological activity of each respective molecule.

APG04, FDH02, or D1B2 proteins are present in specific cell types, e.g., dendritic cells, and the interaction of the protease with a substrate will be important for mediating various aspects of cellular physiology or development. The cellular types which express messages encoding APG02, FDH02, and D1B2 suggest that signals important in cell differentiation and development are mediated by them. See, e.g., Gilbert (1991) *Developmental Biology* (3d ed.) Sinauer Associates, Sunderland, Mass.; Browder, et al. (1991) *Developmental Biology* (3d ed.) Saunders, Philadelphia, Pa.; Russo, et al. (1992) *Development: The Molecular Genetic Approach* Springer-Verlag, New York, N.Y.; and Wilkins (1993) *Genetic Analysis of Animal Development* (2d ed.) Wiley-Liss, New York, N.Y. In particular, the proteases may be necessary for the conversion of pro-proteins to proteins, e.g., cytokine or protein precursors to mature forms, or for proper immunological function, e.g., antigen processing and presentation.

II. Definitions

The term "binding composition" refers to molecules that bind with specificity to APG04, FDH02, or D1B2, respectively, e.g., in an antibody-antigen interaction. However, other compounds, e.g., receptor proteins, may also specifically associate with APG04, FDH02, or D1B2 to the exclusion of other molecules. Typically, the association will be in a natural physiologically relevant protein-protein interaction, either covalent or non-covalent, and may include members of a multiprotein complex, including carrier compounds or dimerization partners. The molecule may be a polymer, or chemical reagent. A functional analog may be a protease with structural modifications, or may be a wholly unrelated molecule, e.g., which has a molecular shape which interacts with the appropriate substrate cleavage determinants.

The term "binding agent:APG04, FDH02 or D1B2 protein complex", as used herein, refers to a complex of a binding agent and an APG04, FDH02, or D1B2 protein that is formed by specific binding of the binding agent to the APG04, FDH02, or D1B2 protein. Specific binding of the binding agent means that the binding agent has a specific binding site that recognizes a site on the APG04, FDH02, or D1B2 protein. For example, antibodies raised to an APG04, FDH02, or D1B2 protein and recognizing an epitope on the APG04, FDH02, or D1B2 protein are capable of forming a binding agent:APG04, FDH02, or D1B2 protein complex by specific binding. Typically, the formation of a binding agent: APG04, FDH02, or D1B2 protein complex allows the measurement of APG04, FDH02, or D1B2 protein in a mixture of other proteins and biologics. The term "antibody:APG04, FDH02, or D1B2 protein complex" refers to an embodiment in which the binding agent is an antibody. The antibody may be monoclonal, polyclonal, or a binding fragment of an antibody e.g., an Fab of F(ab)2 fragment. The antibody will preferably be a polyclonal antibody for cross-reactivity determinations.

"Homologous" nucleic acid sequences, when compared, exhibit significant similarity or identity. The standards for homology in nucleic acids are either measures for homology generally used in the art by sequence comparison and/or phylogenetic relationship, or based upon hybridization conditions. Hybridization conditions are described in greater detail below.

An "isolated" nucleic acid is a nucleic acid, e.g., an RNA, DNA, or a mixed polymer, which is substantially separated from other biologic components which naturally accompany a native sequence, e.g., proteins and flanking genomic sequences from the originating species. The term embraces a nucleic acid sequence which has been removed from its naturally occurring environment, and includes recombinant or cloned DNA isolates and chemically synthesized analogs, or analogs biologically synthesized by heterologous systems. A substantially pure molecule includes isolated forms of the molecule. An isolated nucleic acid will usually. contain homogeneous nucleic acid molecules, but will, in some embodiments, contain nucleic acids with minor sequence heterogeneity. This heterogeneity is typically found at the polymer ends or portions not critical to a desired biological function or activity.

As used herein, the term "APG04, FDH02, or D1B2 protein" shall encompass, when used in a protein context, a protein having amino acid sequences, particularly from the protein motif portions, shown in SEQ ID NO: 2, 4, or 6. In many contexts, a significant fragment of such a protein will be functionally equivalent. The invention also embraces a polypeptide which exhibits similar structure to human APG04, FDH02, or D1B2 protein, e.g., which interacts with APG04, FDH02, or D1B2 specific binding components. These binding components, e.g., antibodies., typically bind to APG04, FDH02, or D1B2 protein with high affinity, e.g., at least about 100 M, usually better than about 30 nM, preferably better than about 10 nM, and more preferably at better than about 3 nM.

The term "polypeptide" or "protein" as used herein includes a significant fragment or segment of protease motif portion of APG04, FDH02, or D1B2 protein, and encompasses a stretch of amino acid residues of at least about 8 amino acids, generally at least about 10 amino acids, more generally at least about 12 amino acids, often at least about 14 amino acids, more often at least about 16 amino acids, typically at least about 18 amino acids, more typically at least about 20 amino acids, usually at least about 22 amino acids, more usually at least about 24 amino acids, preferably at least about 26 amino acids; more preferably at least about 28 amino acids, and, in particularly preferred embodiments, at least about 30 or more amino acids, e.g., 35, 40, 45, 50, 60, 70, 80, etc.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any non-naturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

"Solubility" is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.) W.H. Freeman & Co., San Francisco, Calif.; and Cantor and Schimmel (1980) *Biophysical Chemistry* parts 1–3, W. H. Freeman & Co., San Francisco, Calif. As a crude determination, a sample containing a putatively soluble polypeptide is spun in a standard full sized ultracentrifuge at about 50K rpm for about 10 minutes and soluble molecules will remain in the supernatant. A Soluble particle or polypeptide will typically be less than about 30 S, more typically less than about 15 S, usually less than about 10 S, more usually less than about 6 S, and, in particular embodiments, preferably less than about 4 S, and more preferably less than about 3 S. Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The size and structure of the pqlypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS (cholesteryl hemisuccinate) or CHAPS (3-[3-cholamidopropyl)dimethylammonio]-1-propane sulfonate), or a low enough concentration as to avoid significant disruption of structural or physiological properties of the protein.

"Substantially pure" in a protein context typically means that the protein is isolated from other contaminating proteins, nucleic acids, and other biologicals derived from the original source organism. Purity, or "isolation" may be assayed by standard methods, and will ordinarily be at least about 50% pure, more ordinarily at least about 60% pure, generally at least about 70% pure, more generally at least about 80% pure, often at least about 85% pure, more often at least about 90% pure, preferably at least about 95% pure, more preferably at least about 98% pure, and in most preferred embodiments, at least 99% pure. Similar concepts apply, e.g., to antibodies or nucleic acids.

"Substantial similarity" in the nucleic acid sequence comparison context means either that the segments, or their complementary strands, when compared, are identical when optimally aligned, with appropriate nucleotide insertions or deletions, in at least about 50% of the nucleotides, generally at least about 56%, more generally at least about 59%, ordinarily at least about 62%, more ordinarily at least about 65%, often at least about 68%, more often at least about 71%, typically at least about 74%, more typically at least about 77%, usually at least about 80%, more usually at least about 85%, preferably at least about 90%, more preferably at least about 95 to 98% or more, and in particular embodiments, as high at about 99% or more of the nucleotides. Alternatively, substantial similarity exists when the segments will hybridize under selective hybridization conditions, to a strand, or its complement, typically using a sequence derived from SEQ ID NO: 1, 3, or 5. Typically, selective hybridization will occur when there is at least about 55% similarity over a stretch of at least about 30 nucleotides, preferably at least about 65% over a stretch of at least about 25 nucleotides, more preferably at least about 75%, and most preferably at least about 90% over about 20 nucleotides. See Kanehisa (1984) *Nuc. Acids Res.* 12:203–213. The length of similarity comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides, e.g., 150, 200, etc.

"Stringent conditions", in referring to homology or substantial similarity in the hybridization context, will be stringent combined conditions of salt, temperature, organic solvents, and other parameters, typically those controlled in hybridization reactions. The combination of parameters is more important than the measure of any single parameter. See, e.g., Wetmur and Davidson (1968) *J. Mol. Biol.* 31:349–370. A nucleic acid probe which binds to a target nucleic acid under stringent conditions is specific for said target nucleic acid. Such a probe is typically more than 11 nucleotides in length, and is sufficiently identical or complementary to a target nucleic acid over the region specified by the sequence of the probe to bind the target under stringent hybridization conditions.

APG04, FDH02, or D1B2 proteins from other mammalian species can be cloned and isolated by cross-species hybridization of closely related species. See, e.g., below. Similarity may be relatively low between distantly related species, and thus hybridization of relatively closely related species is advisable. Alternatively, preparation of an antibody preparation which exhibits less species specificity may be useful in expression cloning approaches.

The phrase "specifically binds to an antibody" or "specifically immunoreactive with"; when referring to a protein or peptide, refers to a binding reaction which is determinative of the presence of the protein in the presence of a heterogeneous population of proteins and other biological components. Thus, under designated immunoassay conditions, the specified antibodies bind to a particular protein and do not significantly bind other proteins present in the sample. Specific binding to an antibody under such conditions may require an antibody that is selected for its specificity for a particular protein. For example, antibodies raised to the human APG04, FDH02, or D1B2 protein immunogen with the amino acid sequence depicted in SEQ ID NO: 2, 4, or 6 can be selected by immunoaffinity or similar methods to obtain antibodies specifically immunoreactive with APG04, FDH02, or D1B2 proteins and not with other proteins.

III. Nucleic Acids

APG04, FDH02, or D1B2 proteins are exemplary of a larger class of structurally and functionally related proteins. These proteins will serve to cleave various proteins produced or processed by various cell types. The preferred embodiments, as disclosed, will be useful in standard procedures to isolate genes from different individuals or other species, e.g., warm blooded animals, such as birds and mammals. Cross hybridization will allow isolation of related genes encoding proteins from individuals, strains, or species. A number of different approaches are available to successfully isolate a suitable nucleic acid clone based upon the information provided herein. Southern blot hybridization studies can qualitatively determine the presence of homologous genes in human, monkey, rat, dog, cow, and rabbit genomes under specific hybridization conditions.

Complementary sequences will also be used as probes or primers. Based upon identification of the likely amino terminus, other peptides should be particularly useful, e.g., coupled with anchored vector or poly-A complementary PCR techniques or with complementary DNA of other peptides.

Techniques for nucleic acid manipulation of genes encoding APG04, FDH02, or D1B2 proteins, such as subcloning nucleic acid sequences encoding polypeptides into expression vectors, labelling probes, DNA hybridization, and the like are described generally in Sambrook, et al. (1989) *Molecular Cloning: A Laboratory Manual* (2nd ed.) Vol. 1–3, Cold Spring Harbor Laboratory, Cold Spring Harbor Press, N.Y., which is incorporated herein by reference. This manual is hereinafter referred to as "Sambrook, et al.".

There are various methods of isolating DNA sequences encoding APG04, FDH02, or D1B2 proteins. For example, DNA is isolated from a genomic or cDNA library using labeled oligonucleotide probes having sequences identical or complementary to the sequences disclosed herein. Full-length probes may be used, or oligonucleotide probes may be generated by comparison of the sequences disclosed. Such probes can be used directly in hybridization assays to isolate DNA encoding APG04, FDH02, or D1B2 proteins, or probes can be designed for use in amplification techniques such as PCR, for the isolation of DNA encoding APG04, FDH02, or D1B2 proteins.

To prepare a cDNA library, mRNA is isolated from cells which expresses an APG04, FDH02, or D1B2 protein. cDNA is prepared from the mRNA and ligated into a recombinant vector. The vector is transfected into a recombinant host for propagation, screening, and cloning. Methods for making and screening cDNA libraries are well known. See Gubler and Hoffman (1983) *Gene* 25:263–269 and Sambrook, et al.

For a genomic library, the DNA can be extracted from tissue and either mechanically sheared or enzymatically digested to yield fragments of about 12–20 kb. The fragments are then separated by gradient centrifugation and cloned in bacteriophage lambda vectors. These vectors and phage are packaged in vitro, as described in Sambrook, et al. Recombinant phage are analyzed by plaque hybridization as described in Benton and Davis (1977) *Science* 196:180–182. Colony hybridization is carried out as generally described in e.g., Grunstein, et al. (1975) *Proc. Natl. Acad. Sci. USA.* 72:3961–3965.

DNA encoding an APG04, FDH02, or D1B2 protein can be identified in either cDNA or genomic libraries by its ability to hybridize with the nucleic acid probes described herein, e.g., in colony or plaque hybridization assays. The corresponding DNA regions are isolated by standard methods familiar to those of skill in the art. See, e.g., Sambrook, et al.

Various methods of amplifying target sequences, such as the polymerase chain reaction, can also be used to prepare DNA encoding APG04, FDH02, or D1B2 proteins. Polymerase chain reaction (PCR) technology is used to amplify such nucleic acid sequences directly from mRNA, from cDNA, and from genomic libraries or cDNA libraries. The isolated sequences encoding APG04, FDH02, or D1B2 proteins may also be used as templates for PCR amplification.

Typically, in PCR techniques, oligonucleotide primers complementary to two 5' regions in the DNA region to be amplified are synthesized. The polymerase chain reaction is then carried out using the two primers. See Innis, et al. (eds.) (1990) *PCR Protocols: A Guide to Methods and Applications* Academic Press, San Diego, Calif. Primers can be selected to amplify the entire regions encoding a full-length human APG04, FDH02, or D1B2 protein or to amplify smaller DNA segments as desired. Once such regions are PCR-amplified, they can be sequenced and oligonucleotide probes can be prepared from sequence obtained using standard techniques. These probes can then be used to isolate DNA's encoding APG04, FDH02, or D1B2 proteins.

Oligonucleotides for use as probes are usually chemically synthesized according to the solid phase phosphoramidite triester method first described by Beaucage and Carruthers (1983) *Tetrahedron Lett.* 22(20):1859–1862, or using an automated synthesizer, as described in Needham-VanDevanter, et al. (1984) *Nucleic Acids Res.* 12:6159–6168. Purification of oligonucleotides is performed e.g., by native acrylamide gel electrophoresis or by anion-exchange HPLC as described in Pearson and Regnier (1983) *J. Chrom.* 255:137–149. The sequence of the synthetic oligonucleotide can be verified using, e.g., the chemical degradation method of Maxam, A. M. and Gilbert, W. in Grossman, L. and Moldave (eds.) (1980) *Methods in Enzymology* 65:499–560 Academic Press, New York.

An isolated nucleic acid encoding a human APG04, FDH02, or D1B2 protein was identified. The nucleotide sequence, corresponding open reading frames, and mature peptides are provided in Tables 1, 2, or 3 and SEQ ID NO: 1–6.

This invention provides isolated DNA or fragments to encode an APG04, FDH02, or D1B2 protein or specific fragment thereof. In addition, this invention provides isolated or recombinant DNA which encodes a protein or polypeptide, and which is capable of hybridizing under appropriate conditions, e.g., high stringency, with the DNA sequences described herein. Said biologically active protein or polypeptide can be a functional protease segment, or fragment, and have an amino acid sequence as disclosed in SEQ ID NO: 2, 4, or 6. Preferred embodiments will be full length natural sequences, from isolates, or proteolytic fragments thereof. Further, this invention contemplates the use of isolated or recombinant DNA, or fragments thereof, which encode proteins which exhibit high measures of identity to an APG04, FDH02, or D1B2 protein, or which were isolated using cDNA encoding an APG04, FDH02, or D1B2 protease protein as a probe. The isolated DNA can have the respective regulatory sequences in the 5' and 3' flanks, e.g., promoters, enhancers, poly-A addition signals, and others.

IV. Making human APG04, FDH02, or D1B2 proteins

DNAs which encode an APG04, FDH02, or D1B2 protein or fragments thereof can be obtained by chemical synthesis, screening cDNA libraries, or by screening genomic libraries prepared from a wide variety of cell lines or tissue samples.

These DNAs can be expressed in a wide variety of host cells for the synthesis of a full-length protein or fragments which can in turn, e.g., be used to generate polyclonal or monoclonal antibodies; for binding studies; for construction and expression of modified molecules; and for structure/function studies. Each of APG04, FDH02, or D1B2, or its fragments can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigen, e.g., APG04, FDH02, or D1B2, or portions thereof, may be expressed as fusions with other proteins or possessing an epitope tag.

Expression vectors are typically self-replicating DNA or RNA constructs containing the desired antigen gene or its fragments, usually operably linked to appropriate genetic control elements that are recognized in a suitable host cell. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently from the host cell.

The vectors of this invention contain DNAs which encode an APG04, FDH02, or D1B2 protein, or a significant fragment thereof, typically encoding, e.g., a biologically active polypeptide, or protein. The DNA can be under the control of a viral promoter and can encode a selection marker. This invention further contemplates use of such expression vectors which are capable of expressing eukaryotic cDNA coding for an APG04, FDH02, or D1B2 protein in a prokaryotic or eukaryotic host, where the vector is compatible with the host and where the eukaryotic cDNA coding for the protein is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the protein or its fragments in various hosts using vectors that do not contain a replication origin that is recognized by the host cell. It is also possible to use vectors that cause integration of an APG04, FDH02, or D1B2 protein gene or its fragments into the host DNA by recombination, or to integrate a promoter which controls expression of an endogenous gene.

Vectors, as used herein, contemplate plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector, but many other forms of vectors which serve an equivalent function are suitable for use herein. See, e.g., Pouwels, et al. (1985 and Supplements) *Cloning Vectors: A Laboratory Manual* Elsevier, N.Y.; and Rodriquez, et al. (eds.) (1988) *Vectors: A Survey of Molecular Cloning Vectors and Their Uses* Buttersworth, Boston, Mass.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and *Pichia*, and species of the genus *Dictyostelium*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or its derivatives. Vectors that can be used to express APG04, FDH02, or D1B2 proteins or fragments thereof include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in Rodriguez and Denhardt (eds.) *Vectors: A Survey of Molecular Cloning Vectors and Their Uses* 10:205–236 Buttersworth, Boston, Mass.

Lower eukaryotes, e.g., yeasts and Dictyostelium, may be transformed with APG04, FDH02, or D1B2 protein sequence containing vectors. For purposes of this invention, the most common lower eukaryotic host is the baker's yeast, *Saccharomyces cerevisiae*. It will be used generically to represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are typically the preferred host cells for expression of the functionally active APG04, FDH02, or D1B2 protease protein. In principle, many higher eukaryotic tissue culture cell lines may be used, e.g., insect baculovirus expression systems, whether from an invertebrate or vertebrate source. However, mammalian cells are preferred to achieve proper processing, both cotranslationally and posttranslationally. Transformation or transfection and propagation of such cells is routine. Useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (e.g., if genomic DNA is used), a polyadenylation site, and a transcription termination site. These vectors also may contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pcDNA1; pCD, see Okayama, et al. (1985) *Mol. Cell Biol.* 5:1136–1142; pMC1neo Poly-A, see Thomas, et al. (1987) *Cell* 51:503–512; and a baculovirus vector such as pAC 373 or pAC 610.

It is likely that APG04, FDH02, or D1B2 protein need not be glycosylated to elicit biological responses. However, it will occasionally be desirable to express an APG04, FDH02, or D1B2 protein polypeptide in a system which provides a specific or defined glycosylation pattern. In this case, the usual pattern will be that provided naturally by the expression system. However, the pattern will be modifiable by exposing the polypeptide, e.g., in unglycosylated form, to appropriate glycosylating proteins introduced into a heterologous expression system. For example, an APG04, FDH02, or D1B2 protein gene may be co-transformed with one or more genes encoding mammalian or other glycosylating enzymes. It is further understood that over glycosylation may be detrimental to APG04, FDH02, or D1B2 protein biological activity, and that one of skill may perform routine testing to optimize the degree of glycosylation which confers optimal biological activity.

An APG04, FDH02, or D1B2 protein, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochem. Biophys. Acta* 988:427–454; Tse, et al. (1985) *Science* 230:1003–1008; and Brunner, et al. (1991) *J. Cell Biol.* 114:1275–1283.

Now that APG04, FDH02, or D1B2 proteins have been characterized, fragments or derivatives thereof can be prepared by conventional processes for synthesizing peptides. These include processes such as are described in Stewart and Young (1984) *Solid Phase Peptide Synthesis* Pierce Chemical Co., Rockford, Ill.; Bodanszky and Bodanszky (1984) *The Practice of Peptide Synthesis* Springer-Verlag, New York, N.Y.; and Bodanszky (1984) *The Principles of Peptide Synthesis* Springer-Verlag, New York, N.Y. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The prepared protein and fragments thereof can be isolated and purified from the reaction mixture by means of peptide separation, for example, by extraction, precipitation, electrophoresis and various forms of chromatography, and the like. The APG04, FDH02, or D1B2 proteins of this invention can be obtained in varying degrees of purity depending upon its desired use. Purification can be accomplished by use of known protein purification techniques or by the use of the antibodies or binding partners herein described, e.g., in immunoabsorbant affinity chromatography. This immunoabsorbant affinity chromatography is carried out by first linking the antibodies to a solid support and then contacting the linked antibodies with solubilized lysates of appropriate source cells, lysates of other cells expressing the ligand, or lysates or supernatants of cells producing the APG04, FDH02, or D1B2 proteins as a result of recombinant DNA techniques, see below.

Multiple cell lines may be screened for one which expresses an APG04, FDH02, or D1B2 protein at a high level compared with other cells. Various cell lines, e.g., a mouse thymic stromal cell line TA4, is screened and selected for its favorable handling properties. Natural APG04, FDH02, or D1B2 proteins can be isolated from natural sources, or by expression from a transformed cell using an appropriate expression vector. Purification of the expressed protein is achieved by standard procedures, or may be combined with engineered means for effective purification at high efficiency from cell lysates or supernatants. Epitope or other tags, e.g., FLAG or $His_6$ segments, can be used for such purification features.

V. Antibodies

Antibodies can be raised to various APG04, FDH02, or D1B2 proteins, including individual, polymorphic, allelic, strain, or species variants, and fragments thereof, both in their naturally occurring (full-length) forms and in their recombinant forms. Additionally, antibodies can be raised to APG04, FDH02, or D1B2 proteins in either their active forms or in their inactive, e.g., denatured, forms. Anti-idiotypic antibodies may also be used.

A. Antibody Production

A number of immunogens may be used to produce antibodies specifically reactive with APG04, FDH02, or D1B2 proteins. Recombinant protein is the preferred immunogen for the production of monoclonal or polyclonal antibodies. Naturally occurring protein may also be used either in pure or impure form. Synthetic peptides, made using the human APG04, FDH02, or D1B2 protein sequences described herein, may also used as an immunogen for the production of antibodies to APG04, FDH02, or D1B2 proteins. Recombinant protein can be expressed in eukaryotic or prokaryotic cells as described herein, and purified as described. Naturally folded or denatured material can be used, as appropriate, for producing antibodies. Either monoclonal or polyclonal antibodies may be generated for subsequent use in immunoassays to measure the protein.

Methods of producing polyclonal antibodies are known to those of skill in the art. Typically, an immunogen, preferably a purified protein, is mixed with an adjuvant and animals are immunized with the mixture. The animal's immune response to the immunogen preparation is monitored by taking test bleeds and determining the titer of reactivity to the APG04, FDH02, or D1B2 protein of interest. When appropriately high titers of antibody to the immunogen are obtained, usually after repeated immunizations, blood is collected from the animal and antisera are prepared. Further fractionation of the antisera to enrich for antibodies reactive to the protein can be done if desired. See, e.g., Harlow and Lane; or Coligan.

Monoclonal antibodies may be obtained by various techniques familiar to those skilled in the art. Typically, spleen cells from an animal immunized with a desired antigen are immortalized, commonly by fusion with a myeloma cell (see, Kohler and Milstein (1976) *Eur. J. Immunol.* 6:511–519, incorporated herein by reference). Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) *Science* 246:1275–1281.

Antibodies, including binding fragments and single chain versions, against predetermined fragments of APG04, FDH02, or D1B2 proteins can be raised by immunization of animals with conjugates of the fragments with carrier proteins as described above. Monoclonal antibodies are prepared from cells secreting the desired antibody. These antibodies can be screened for binding to normal or defective APG04, FDH02, or D1B2 protein, or screened for agonistic or antagonistic activity, e.g., mediated through a receptor. These monoclonal antibodies will usually bind with at least a $K_D$ of about 1 nM, more usually at least about 300 $\mu$M, typically at least about 10 $\mu$M, more typically at least about 30 $\mu$M, preferably at least about 10 $\mu$M, and more preferably at least about 3 $\mu$M or better.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.) Lange Medical Publications, Los Altos, Calif., and references cited therein; Harlow and Lane (1988) *Antibodies: A Laboratory Manual* CSH Press; Goding (1986) *Monoclonal Antibodies: Principles and Practice* (2d ed.) Academic Press, New York, N.Y.; and particularly in Kohler and Milstein (1975) *Nature* 256:495–497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, e.g., Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen, et al. (1989) *Proc. Nat'l Acad. Sci. USA* 86:10029–10033.

The antibodies of this invention are useful for affinity chromatography in isolating APG04, FDH02, or D1B2 protein. Columns can be prepared where the antibodies are linked to a solid support, e.g., particles, such as agarose (Amersham Pharmacia Biotech, Piscataway, N.J.), SEPHADEX, a gel filtration medium (Amersham Pharmacia Biotech), or the like, where a cell lysate or supernatant may be passed through the column, the column washed, followed by increasing concentrations of a mild denaturant, whereby purified APG04, FDH02, or D1B2 protein will be released.

Other antibodies may block enzymatic activity. The antibodies may also be used to screen expression libraries for particular expression products. Usually the antibodies used in such a procedure will be labeled with a moiety allowing easy detection of presence of antigen by antibody binding.

Antibodies to APG04, FDH02, or D1B2 proteins may be used for the identification of cell populations expressing APG04, FDH02, or D1B2 protein. By assaying the expression products of cells expressing APG04, FDH02, or D1B2 proteins it is possible to diagnose disease, e.g., immune-compromised conditions.

Antibodies raised against each APG04, FDH02, or D1B2 protein will also be useful to raise anti-idiotypic antibodies. These will be useful in detecting or diagnosing various immunological conditions related to expression of the respective antigens.

B. Immunoassays

A particular protein can be measured by a variety of immunoassay methods. For a review of immunological and immunoassay procedures in general, see Stites and Terr (eds.) (1991) *Basic and Clinical Immunology* (7th ed.). Moreover, the immunoassays of the present invention can be performed in many configurations, which are reviewed extensively in Maggio (ed.) (1980) *Enzyme Immunoassay* CRC Press, Boca Raton, Fla.; Tijan (1985) "Practice and Theory of Enzyme Immunoassays," *Laboratory Technicues in Biochemistry and Molecular Biology*, Elsevier Science Publishers B.V., Amsterdam; and Harlow and Lane *Antibodies, A Laboratory Manual*, supra, each of which is incorporated herein by reference. See also Chan (ed.) (1987) *Immunoassay: A Practical Guide* Academic Press, Orlando, Fla.; Price and Newman (eds.) (1991) *Principles and Practice of Immunoassays* Stockton Press, NY; and Ngo (ed.) (1988) *Non-isotopic Immunoassays* Plenum Press, NY.

Immunoassays for measurement of APG04, FDH02, or D1B2 proteins or peptides can be performed by a variety of methods known to those skilled in the art. In brief, immunoassays to measure the protein can be either competitive or noncompetitive binding assays. In competitive binding assays, the sample to be analyzed competes with a labeled analyte for specific binding sites on a capture agent bound to a solid surface. Preferably the capture agent is an antibody specifically reactive with APG04, FDH02, or D1B2 proteins produced as described above. The concentration of labeled analyte bound to the capture agent is inversely proportional to the amount of free analyte present in the sample.

In a competitive binding immunoassay, the APG04, FDH02, or D1B2 protein present in the sample competes with labeled protein for binding to a specific binding agent, for example, an antibody specifically reactive with the APG04, FDH02, or D1B2 protein. The binding agent may be bound to a solid surface to effect separation of bound labeled protein from the unbound labeled protein. Alternately, the competitive binding assay may be conducted in liquid phase and a variety of techniques known in the art may be used to separate the bound labelled protein from the unbound labeled protein. Following separation, the amount of bound labeled protein is determined. The amount of protein present in the sample is inversely proportional to the amount of labeled protein binding.

Alternatively, a homogeneous immunoassay may be performed in which a separation step is not needed. In these immunoassays, the label on the protein is altered by the binding of the protein to its specific binding agent. This alteration in the labeled protein results in a decrease or increase in the signal emitted by label, so that measurement of the label at the end of the immunoassay allows for detection or quantitation of the protein.

APG04, FDH02, or D1B2 proteins may also be determined by a variety of noncompetitive immunoassay methods. For example, a two-site, solid phase sandwich immunoassay may be used. In this type of assay, a binding agent for the protein, for example an antibody, is attached to a solid support. A second protein binding agent, which may also be an antibody, and which binds the protein at a different site, is labelled. After binding at both sites on the protein has occurred, the unbound labeled binding agent is removed and the amount of labeled binding agent bound to the solid phase is measured. The amount of labeled binding agent bound is directly proportional to the amount of protein in the sample.

Western blot analysis can be used to determine the presence of APG04, FDH02, or D1B2 proteins in a sample. Electrophoresis is carried out, for example, on a tissue sample suspected of containing the protein. Following electrophoresis to separate the proteins, and transfer of the proteins to a suitable solid support, e.g., a nitrocellulose filter, the solid support is incubated with an antibody reactive with the protein. This antibody may be labeled, or alternatively may be detected by subsequent incubation with a second labeled antibody that binds the primary antibody.

The immunoassay formats described above employ labeled assay components. The label may be coupled directly or indirectly to the desired component of the assay according to methods well known in the art. A wide variety of labels and methods may be used. Traditionally, a radioactive label incorporating $^3$H, $^{125}$I, $^{35}$S, $^{14}$C, or $^{32}$P was used. Non-radioactive labels include ligands which bind to labeled antibodies, fluorophores, chemiluminescent agents, enzymes, and antibodies which can serve as specific binding pair members for a labeled ligand. The choice of label depends on sensitivity required, ease of conjugation with the compound, stability requirements, and available instrumentation. For a review of various labelling or signal producing systems which may be used, see U.S. Pat. No. 4,391,904, which is incorporated herein by reference.

Antibodies reactive with a particular protein can also be measured by a variety of immunoassay methods. For a review of immunological and immunoassay procedures applicable to the measurement of antibodies by immunoassay techniques, see Stites and Terr (eds.) *Basic and Clinical Immunology* (7th ed.) supra; Maggio (ed.) *Enzyme Immunoassay*, supra; and Harlow and Lane *Antibodies, A Laboratory Manual*, supra.

In brief, immunoassays to measure antisera reactive with APG04, FDH02, or D1B2 proteins can be either competitive or noncompetitive binding assays. In competitive binding assays, the sample analyte competes with a labeled analyte for specific binding sites on a capture agent bound to a solid surface. Preferably the capture agent is a purified recombinant APG04, FDH02, or D1B2 protein produced as described above. Other sources of APG04, FDH02, or D1B2 proteins, including isolated or partially purified naturally occurring protein, may also be used. Noncompetitive assays include sandwich assays, in which the sample analyte is bound between two analyte-specific binding reagents. One of the binding agents is used as a capture agent and is bound to a solid surface. The second binding agent is labeled and is used to measure or detect the resultant complex by visual or instrument means. A number of combinations of capture agent and labelled binding agent can be used. A variety of different immunoassay formats, separation techniques, and labels can be also be used similar to those described above for the measurement of APG04, FDH02, or D1B2 proteins.

VI. Purified APG04, FDH02, or D1B2 Proteins

Human APG04, FDH02, or D1B2 protein amino acid sequences are provided in SEQ ID NO: 2, 4, and 6.

Purified protein or defined peptides are useful for generating antibodies by standard methods, as described above. Synthetic peptides or purified protein can be presented to an immune system to generate polyclonal and monoclonal antibodies. See, e.g., Coligan (1991) *Current Protocols in Immunoloogy* Wiley/Greene, NY; and Harlow and Lane (1989) *Antibodies: A Laboratory Manual* Cold Spring Harbor Press, NY, which are incorporated herein by reference.

The specific binding composition can be used for screening an expression library made from a cell line which expresses an APG04, FDH02, or D1B2 protein. Many methods for screening are available, e.g., standard staining of surface expressed ligand, or by panning. Screening of intracellular expression can also be performed by various staining or immunofluorescence procedures. The binding compositions could be used to affinity purify or sort out cells expressing the ligand.

The peptide segments, along with comparison to homologous genes, can also be used to produce appropriate oligonucleotides to screen a library. The genetic code can be used to select appropriate oligonucleotides useful as probes for screening. In combination with polymerase chain reaction (PCR) techniques, synthetic oligonucleotides will be useful in selecting desired clones from a library, including natural allelic and polymorphic variants.

The peptide sequences allow preparation of peptides to generate antibodies to recognize such segments, and allow preparation of oligonucleotides which encode such sequences. The sequence also allows for synthetic preparation, e.g., see Dawson, et al. (1994) *Science* 266:776–779. Since APG04 proteins appear to be secreted proteins, the gene will normally possess an N-terminal signal sequence, which is removed upon processing and secretion, and the putative cleavage site is between amino acids 20 and 21 in SEQ ID NO: 2 and 4, and between amino acids 19 and 20 in SEQ ID NO: 6, though it may be slightly in either direction. Analysis of the structural features in comparison with the most closely related reported sequences has revealed similarities with other proteins, particularly the class of proteins known as proteases.

VII. Physical Variants

This invention also encompasses proteins or peptides having substantial amino acid sequence similarity with an amino acid sequence of an APG04, FDH02, or D1B2 protein. Natural variants include individual, polymorphic, allelic, strain, or species variants. Conservative substitutions in the amino acid sequence will normally preserve most relevant biological activities.

Amino acid sequence similarity, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences include natural polymorphic, allelic, and interspecies variations in each respective protein sequence. Typical homologous proteins or peptides will have from 50–100% similarity (if gaps can be introduced), to 75–100% similarity (if conservative substitutions are included) with the amino acid sequence of the APG04, FDH02, or D1B2 protein. Similarity measures will be at least about 50%, generally at least about 60%, more generally at least about 65%, usually at least about 70%, more usually at least about 75%, preferably at least about 80%, and more preferably at least about 80%, and in particularly preferred embodiments, at least about 85% or more. See also Needleham, et al. (1970) *J. Mol. Biol.* 48:443–453; Sankoff, et al. (1983) *Time Warps. String Edits, and Macromolecules: The Theory and Practice of Seaquence Comparison* Chapter One, Addison-Wesley, Reading, Mass.; and software packages from IntelliGenetics, Mountain View, Calif.; and the University of Wisconsin Genetics Computer Group, Madison, Wis.

Natural nucleic acids encoding mammalian APG04, FDH02, or D1B2 proteins will typically hybridize to the nucleic acid sequence of SEQ ID NO: 1, 3, or 5 under stringent conditions. For example, nucleic acids encoding human APG04, FDH02, or D1B2 proteins will normally hybridize to the nucleic acid of SEQ ID NO: 1, 3, or 5 under stringent hybridization conditions. Generally, stringent conditions are selected to be about 10° C lower than the thermal melting point (Tm) for the probe sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.2 molar at pH 7 and the temperature is at least about 50° C. Other factors may significantly affect the stringency of hybridization, including, among others, base composition and size of the complementary strands, the presence of organic solvents such as formamide, and the extent of base mismatching. A preferred embodiment will include nucleic acids which will bind to disclosed sequences in 50% formamide and 200 mM NaCl at 42° C.

An isolated APG04, FDH02, or D1B2 protein DNA can be readily modified by nucleotide substitutions, nucleotide deletions, nucleotide insertions, and short inversions of nucleotide stretches. These modifications result in novel DNA sequences which encode APG04, FDH02, or D1B2 protein antigens, their derivatives, or proteins having highly similar physiological, immunogenic, or antigenic activity.

Modified sequences can be used to produce mutant antigens or to enhance expression. Enhanced expression may involve gene amplification, increased transcription, increased translation, and other mechanisms. Such mutant APG04, FDH02, or D1B2 protein derivatives include predetermined or site-specific mutations of the respective protein or its fragments. "Mutant APG04, FDH02, or D1B2 protein" encompasses a polypeptide otherwise falling within the homology definition of the human APG04, FDH02, or D1B2 protein as set forth above, but having an amino acid sequence which differs from that of an APG04, FDH02, or D1B2 protein as found in nature, whether by way of deletion, substitution, or insertion. In particular, "site specific mutant APG04, FDH02, or D1B2 protein" generally includes proteins having significant similarity with a protein having a sequence of SEQ ID NO: 2, 4, or 6, and as sharing various biological activities, e.g., antigenic or immunogenic, with those sequences, and in preferred embodiments contain most or all of the disclosed sequence. This applies also to polymorphic variants from different individuals. Similar concepts apply to different APG04, FDH02, or D1B2 proteins, particularly those found in various warm blooded animals, e.g., mammals and birds. As stated before, it is emphasized that descriptions are generally meant to encompass other APG04, FDH02, or D1B2 proteins, not limited to the human embodiments specifically discussed.

Although site specific mutation sites are predetermined, mutants need not be site specific. APG04, FDH02, or D1B2 protein mutagenesis can be conducted by making amino acid insertions or deletions. Substitutions, deletions, insertions, or any combinations may be generated to arrive at a final construct. Insertions include amino- or carboxyl-terminal fusions, e.g. epitope tags. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also, Sambrook, et al. (1989) and Ausubel, et al. (1987 and Supplements). The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an immunoglobulin with an APG04, FDH02, or D1B2 protein polypeptide is a continuous protein molecule having sequences fused in a typical peptide linkage, typically made as a single translation product and exhibiting properties derived from each source peptide. A similar concept applies to heterologous nucleic acid sequences.

In addition, new constructs may be made from combining similar functional domains from other proteins. For example, protein-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992. Thus, new chimeric polypeptides exhibiting new combinations of specificities will result from the functional linkage of protein-binding specificities and other functional domains.

VIII. Binding Agent:APG04, FDH02, or D1B2 Protein Complexes

An APG04, FDH02, or D1B2 protein that specifically binds to or that is specifically immunoreactive with an antibody generated against a defined immunogen, such as an immunogen consisting of the amino acid sequence of SEQ ID NO: 2, 4, or 6, is typically determined in an immunoassay. The immunoassay uses a polyclonal antiserum which was raised to a protein of SEQ ID NO: 2, 4, or 6. This antiserum is selected to have low crossreactivity against other proteases and any such crossreactivity is removed by immunoabsorbtion prior to use in the immunoassay.

In order to produce antisera for use in an immunoassay, the protein of SEQ ID NO: 2, 4, or 6, is isolated as described herein. For example, recombinant protein may be produced in a mammalian cell line. An inbred strain of mice such as balb/c is immunized with the protein of SEQ ID NO: 2, 4, or 6, using a standard adjuvant, such as Freund's adjuvant, and a standard mouse immunization protocol (see Harlow and Lane, supra). Alternatively, a synthetic peptide, preferably near full length, derived from the sequences disclosed herein and conjugated to a carrier protein can be used an immunogen. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against other proteases, using a competitive binding immunoassay such as the one described in Harlow and Lane, supra, at pages 570–573. Preferably two proteases are used in this determination in conjunction with either APG04, FDH02, or D1B2 protein.

Immunoassays in the competitive binding format can be used for the crossreactivity determinations. For example, a protein of SEQ ID NO: 2, 4, or 6 can be immobilized to a solid support. Proteins added to the assay compete with the binding of the antisera to the immobilized antigen. The ability of the above proteins to compete with the binding of the antisera to the immobilized protein is compared to the protein of SEQ ID NO: 2, 4, or 6. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorbtion with the above-listed proteins.

The immunoabsorbed and pooled antisera are then used in a competitive binding immunoassay as described above to compare a second protein to the immunogen protein (e.g., the protein motif of SEQ ID NO: 2, 4, or 6). In order to make this comparison, the two proteins are each assayed at a wide range of concentrations and the amount of each protein required to inhibit 50% of the binding of the antisera to the immobilized protein is determined. If the amount of the second protein required is less than twice the amount of the protein of SEQ ID NO: 2, 4, or 6 that is required, then the second protein is said to specifically bind to an antibody generated to the immunogen.

It is understood that APG04, FDH02, or D1B2 proteins are families of homologous proteins that comprise two or more genes. For a particular gene product, such as the human APG04, FDH02, or D1B2 proteins, the term refers not only to the amino acid sequences disclosed herein, but also to other proteins that are polymorphic, allelic, non-allelic, or species variants. It is also understood that the term "human APG04, FDH02, or D1B2 protein" includes non-natural mutations introduced by deliberate mutation using conventional recombinant technology such as single site mutation, or by excising short sections of DNA encoding APG04, FDH02, or D1B2 proteins, or by substituting new amino acids, or adding new amino acids. Such minor alterations must substantially maintain the immunoidentity of the original molecule and/or its biological activity. Thus, these alterations include proteins that are specifically immunoreactive with a designated naturally occurring APG04, FDH02, or D1B2 protein, for example, the human APG04, FDH02, or D1B2 protein shown in SEQ ID NO: 2, 4, or 6. The biological properties of the altered proteins can be determined by expressing the protein in an appropriate cell line and measuring, e.g., a chemotactic effect. Particular protein modifications considered minor would include conservative substitution of amino acids with similar chemical properties, as described above for APG04, FDH02, or D1B2 protein families as a whole. By aligning a protein optimally with the protein of SEQ ID NO: 2, 4, or 6, and by using the conventional immunoassays described herein to determine immunoidentity, or by using lymphocyte chemotaxis assays, one can determine the protein compositions of the invention.

IX. Functional Variants

The blocking of physiological response to APG04, FDH02, or D1B2 protein may result from the inhibition of enzymatic activity of the protein against its substrate, e.g., through competitive inhibition. Thus, in vitro assays of the present invention will often use isolated protein, membranes from cells expressing a recombinant membrane associated proteins, soluble fragments comprising enzymatically active segments of these proteins, or fragments attached to solid phase substrates. These assays will also allow for the diagnostic determination of the effects of either binding segment mutations and modifications, or protein mutations and modifications, e.g., protein analogs. This invention also contemplates the use of competitive drug screening assays, e.g., where neutralizing antibodies to antigen or receptor fragments compete with a test compound for binding to the protein. In this manner, the antibodies can be used to detect the presence of a polypeptide which shares one or more antigenic binding sites of the protein and can also be used to occupy binding sites on the protein that might otherwise interact with a receptor.

"Derivatives" of APG04, FDH02, or D1B2 proteins include amino acid sequence mutants, glycosylation variants, and covalent or aggregate conjugates with other chemical moieties. Covalent derivatives can be prepared by linkage of functionalities to groups which are found in APG04, FDH02, or D1B2 protein amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine, or other moieties, including ribosyl groups or cross-linking reagents.

A major group of derivatives are covalent conjugates of the APG04, FDH02, or D1B2 protein or fragments thereof with other proteins or polypeptides. These derivatives can be synthesized in recombinant culture such as N- or C-terminal fusions or by the use of agents known in the art for their usefulness in cross-linking proteins through reactive side groups. Preferred protein derivatization sites with cross-linking agents are at free amino groups, carbohydrate moieties, and cysteine residues.

Fusion polypeptides between human APG04, FDH02, or D1B2 proteins and other homologous or heterologous proteins are also provided. Many growth factors and cytokines are homodimeric entities, and a repeat construct may have various advantages, including lessened susceptibility to proteolytic degradation. Moreover, many receptors require dimerization to transduce a signal, and various dimeric proteins or domain repeats can be desirable. Heterologous polypeptides may be fusions between different surface markers, resulting in, e.g., a hybrid protein exhibiting receptor binding specificity. Likewise, heterologous fusions may be constructed which would exhibit a combination of properties or activities of the derivative proteins. Typical examples are fusions of a reporter polypeptide, e.g., luciferase, with a segment or domain of a protein, e.g., a receptor-binding segment, so that the presence or location of the fused protein may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, and yeast alpha mating factor. See, e.g., Godowski, et al. (1988) *Science* 241:812–816.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

This invention also contemplates the use of derivatives of APG04, FDH02, or D1B2 proteins other than variations in amino acid sequence or glycosylation. Such derivatives may involve covalent or aggregative association with chemical moieties. These derivatives generally fall into the three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of ligands or other binding ligands. For example, an APG04, FDH02, or D1B2 protein can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of anti-APG04, -FDH02, or -D1B2 protein antibodies or its receptor. The APG04, FDH02, or D1B2 proteins can also be labeled with a detectable group, e.g., radioiodinated by the chloramine T procedure, covalently bound to rare earth chelates, or conjugated to another fluorescent moiety for use in diagnostic assays. Purification of APG04, FDH02, or D1B2 proteins may be effected by immobilized antibodies or receptor.

Isolated APG04, FDH02, or D1B2 protein genes will allow transformation of cells lacking expression of corresponding APG04, FDH02, or D1B2 proteins, e.g., either species types or cells which lack corresponding proteins and exhibit negative background activity. Expression of transformed genes will allow isolation of antigenically pure cell lines, with defined or single specie variants. This approach will allow for more sensitive detection and discrimination of the physiological effects of APG04, FDH02, or D1B2 protein substrate proteins. Subcellular fragments, e.g., cytoplasts or membrane fragments, can be isolated and used.

X. Uses

The present invention provides reagents which will find use in diagnostic applications as described elsewhere herein, e.g., in the general description for developmental abnormalities, or below in the description of kits for diagnosis.

APG04, FDH02, or D1B2 protein nucleotides, e.g., human APG04, FDH02, or D1B2 protein DNA or RNA, may be used as a component in a forensic assay. For instance, the nucleotide sequences provided may be labeled using, e.g., $^{32}P$ or biotin and used to probe standard restriction fragment polymorphism blots, providing a measurable character to aid in distinguishing between individuals. Such probes may be used in well-known forensic techniques such as genetic fingerprinting. In addition, nucleotide probes made from APG04, FDH02, or D1B2 protein sequences may be used in situ assays to detect chromosomal abnormalities.

Antibodies and other binding agents directed towards APG04, FDH02, or D1B2 proteins or nucleic acids may be used to purify the corresponding APG04, FDH02, or D1B2 protein molecule. As described in the Examples below, antibody purification of APG04, FDH02, or D1B2 protein components is both possible and practicable. Antibodies and other binding agents may also be used in a diagnostic fashion to determine whether APG04, FDH02, or D1B2 protein components are present in a tissue sample or cell population using well-known techniques described herein. The ability to attach a binding agent to an APG04, FDH02, or D1B2 protein provides a means to diagnose disorders associated with APG04, FDH02, or D1B2 protein misregulation. Antibodies and other APG04, FDH02, or D1B2 protein binding agents may also be useful as histological markers. As described in the examples below, APG04, FDH02, or D1B2 protein expression is limited to specific tissue types. By directing a probe, such as an antibody or nucleic acid to an APG04, FDH02, or D1B2 protein it is possible to use the probe to distinguish tissue and cell types in situ or in vitro.

This invention also provides reagents with significant therapeutic value. The APG04, FDH02, or D1B2 protein (naturally occurring or recombinant), fragments thereof, and antibodies thereto, along with compounds identified as having binding affinity to an APG04, FDH02, or D1B2 protein, are useful in the treatment of conditions associated with abnormal physiology or development, including abnormal proliferation, e.g., cancerous conditions, or degenerative conditions. Abnormal proliferation, regeneration, degeneration, and atrophy may be modulated by appropriate therapeutic treatment using the compositions provided herein. The APG04, FDH02, or D1B2 proteins likely play a role in regulation or development of hematopoietic cells, e.g., lymphoid cells, which affect immunological responses. Thus, for example, an antagonist of an APG04, FDH02, or D1B2 protein could be useful in blocking the conversion of an immature or inactive immunologically relevant pro-protein to the mature or active form. Since these proteases were derived from dendritic cells, antagonists could also be important in preventing antigen processing and/or subsequent presentation.

Other abnormal developmental conditions are known in cell types shown to possess APG04, FDH02, or D1B2 protein mRNA by northern blot analysis. See Berkow (ed.) *The Merck Manual of Diagnosis and Therapy*, Merck & Co., Rahway, N.J.; and Thorn, et al. *Harrison's Principles of Internal Medicine*, McGraw-Hill, NY. Developmental or functional abnormalities, e.g., of the immune system, cause significant medical abnormalities and conditions which may be susceptible to prevention or treatment using compositions provided herein.

Recombinant APG04, FDH02, or D1B2 protein antibodies can be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using antibodies or receptor or fragments thereof can identify compounds having binding affinity to APG04, FDH02, or D1B2 protein, including isolation of associated components. Subsequent biological assays can then be utilized to determine if the compound has intrinsic protease blocking activity. Likewise, a compound having intrinsic stimulating activity might activate the activity of an APG04, FDH02, or D1B2 protein. This invention further contemplates the therapeutic use of antibodies to APG04, FDH02, or D1B2 protein as antagonists. This approach should be particularly useful with other APG04, FDH02, or D1B2 protein polymorphic or species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacoloaical Bases of Therapeutics* (8th ed.) Pergamon Press; and (1990) *Remington's Pharmaceutical Sciences* (17th ed.) Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will. include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

APG04, FDH02, or D1B2 proteins, fragments thereof; antibodies to it or its fragments; antagonists; and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacoloaical Bases of Therapeutics* (8th ed.) Pergamon Press; and (1990) *Reminaton's Pharmaceutical Sciences* (17th ed.) Mack Publishing Co., Easton, Pa.; Avis, et al. (eds.) (1993) *Pharmaceutical Dosaae Forms: Parenteral Medications* Dekker, NY; Lieberman, et al. (eds.) (1990) *Pharmaceutical Dosage Forms: Tablets* Dekker, NY; and Lieberman, et al. (eds.) (1990) *Pharmaceutical Dosaae Forms: Disperse Systems* Dekker, NY. The therapy of this invention may be combined with or used in association with other therapeutic agents.

Both the naturally occurring and the recombinant forms of the APG04, FDH02, or D1B2 proteins of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767–773, and other descriptions of chemical diversity libraries, which describe means for testing of binding affinity by a plurality of compounds. The development of suitable assays can be greatly facilitated by the availability of large amounts of purified, soluble APG04, FDH02, or D1B2 protein as provided by this invention.

For example, antagonists can normally be found once the protein has been structurally defined. Testing of potential protein analogs is now possible upon the development of highly automated assay methods using a purified receptor. In particular, new agonists and antagonists will be discovered by using screening techniques described herein. Of particular importance are compounds found to have a combined blockage activity for multiple APG04, FDH02, or D1B2 protein substrates, e.g., compounds which can serve as antagonists for polymorphic or species variants of an APG04, FDH02, or D1B2 protein.

This invention is particularly useful for screening compounds by using recombinant protein in a variety of drug screening techniques. The advantages of using a recombinant protein in screening for specific ligands include: (a) improved renewable source of the APG04, FDH02, or D1B2 protein from a specific source; (b) potentially greater number of ligands per cell giving better signal to noise ratio in assays; and (c) species variant specificity (theoretically giving greater biological and disease specificity).

One method of drug screening utilizes eukaryotic or prokaryotic host cells which are stably transformed with recombinant DNA molecules expressing an APG04, FDH02, or D1B2 protein substrate. Cells may be isolated which express a substrate in isolation from any others. Such cells, either in viable or fixed form, can be used for standard enzyme/substrate cleavage assays. See also, Parce, et al. (1989) *Science* 246:243–247; and Owicki, et al. (1990) *Proc. Nat'l Acad. Sci. USA* 87:4007–4011, which describe sensitive methods to detect cellular responses. Competitive assays are particularly useful, where the cells (source of APG04, FDH02, or D1B2 protein) ate contacted and incubated with a labeled antibody having known binding affinity to the protein, such as $^{125}$-antibody, and a test sample whose binding affinity to the binding composition is being measured. The bound and free labeled binding compositions are then separated to assess the degree of antigen binding. The amount of test compound bound is inversely proportional to the amount of labeled receptor binding to the known source. Any one of numerous techniques can be used to separate bound from free antigen to assess the degree of ligand binding. This separation step could typically involve a procedure such as adhesion to filters followed by washing, adhesion to plastic followed by washing, or centrifugation of the cell membranes. Viable cells could also be used to screen for the effects of drugs on APG04, FDH02, or D1B2 protein mediated functions, e.g., substrate cleavage, and others. Some detection methods allow for elimination of a separation step, e.g., a proximity sensitive detection system.

Another method utilizes membranes from transformed eukaryotic or prokaryotic host cells as the source of an APG04, FDH02, or D1B2 protein. These cells are stably transformed with DNA vectors directing the expression of an APG04, FDH02, or D1B2 protein, e.g., an engineered membrane bound form. Essentially, the membranes would be prepared from the cells and used in a protein/substrate cleavage assay such as the competitive assay set forth above.

Still another approach is to use solubilized, unpurified or solubilized, purified APG04, FDH02, or D1B2 protein from transformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to an APG04, FDH02, or D1B2 protein, e.g., an antibody, is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al., supra. Then all the pins are reacted with solubilized, unpurified or solubilized, purified APG04, FDH02, or D1B2 protein antibody, and washed. The next step involves detecting bound APG04, FDH02, or D1B2 protein antibody.

Rational drug design may also be based upon structural studies of the molecular shapes of the APG04, FDH02, or D1B2 protein and other effectors or analogs. See, e.g., Langone (1991) *Methods Enzymol.*, Vols. 202 & 203, Molecular Design and Modeling, Parts A & B, Academic Press, San Diego, Calif. Effectors may be other proteins which mediate other functions in response to antigen binding, or other proteins which normally interact with the substrate. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography* Academic Press, NY.

A purified APG04, FDH02, or D1B2 protein can be coated directly onto plates for use in the aforementioned drug screening techniques. However, non-neutralizing antibodies to these antigens can be used as capture antibodies to immobilize the respective antigen on the solid phase.

XI. Kits

This invention also contemplates use of APG04, FDH02, or D1B2 proteins, fragments thereof, peptides, and their fusion products in a variety of diagnostic kits and methods for detecting the presence of APG04, FDH02, or D1B2 protein or an APG04, FDH02, or D1B2 protein substrate. Typically the kit will have a compartment containing either a defined APG04, FDH02, or D1B2 peptide or gene segment or a reagent which recognizes one or the other, e.g., receptor fragments or antibodies.

A kit for determining the binding affinity of a test compound to an APG04, FDH02, or D1B2 protein would typically comprise a test compound; a labeled compound, e.g., an antibody having known binding affinity for the APG04, FDH02, or D1B2 protein; a source of APG04, FDH02, or D1B2 protein (naturally occurring or recombinant); and a means for separating bound from free labeled compound, such as a solid phase for immobilizing the APG04, FDH02, or D1B2 protein. Once compounds are screened, those having suitable binding affinity to the APG04, FDH02, or D1B2 protein can be evaluated in suitable biological assays, as are well known in the art, to determine whether they act as agonists or antagonists to the substrate. The availability of recombinant APG04, FDH02, or D1B2 polypeptides also provide well defined standards for calibrating such assays.

A preferred kit for determining the concentration of, for example, an APG04, FDH02, or D1B2 protein in a sample would typically comprise a labeled compound, e.g., antibody, having known binding affinity for the APG04, FDH02, or D1B2 protein, a source of APG04, FDH02, or D1B2 protein (naturally occurring or recombinant), and a means for separating the bound from free labeled compound, for example, a solid phase for immobilizing the APG04, FDH02, or D1B2 protein. Compartments containing reagents, and instructions, will normally be provided.

Antibodies, including antigen binding fragments, specific for the APG04, FDH02, or D1B2 protein, or fragments thereof, are useful in diagnostic applications to detect the presence of elevated levels of APG04, FDH02, or D1B2 protein and/or its fragments. Such diagnostic assays can employ lysates, live cells, fixed cells, immunofluorescence, cell cultures, body fluids, and further can involve the detection of antigens related to the ligand in serum, or the like. Diagnostic assays may be homogeneous (without a separation step between free reagent and antigen-APG04, -FDH02, or -D1B2 protein complex) or heterogeneous (with a separation step). Various commercial assays exist, such as radio-immunoassay (RIA), enzyme-linked immunosorbentassay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to an APG04, FDH02, or D1B2 protein or to a particular fragment thereof. Similar assays have also been extensively discussed in the literature. See, e.g., Harlow and Lane (1988) *Antibodies: A Laboratory Manual*, CSH Press, NY; Chan (ed.) (1987) *Immunoassay: A Practical Guide* Academic Press, Orlando, Fla.; Price and Newman (eds.) (1991) *Principles and Practice of Immunoassay* Stockton Press, NY; and Ngo (ed.) (1988) *Nonisotopic Immunoassay* Plenum Press, NY.

Anti-idiotypic antibodies may have similar use to diagnose presence of antibodies against an APG04, FDH02, or D1B2 protein, as such may be diagnostic of various abnormal states. For example, overproduction of APG04, FDH02, or D1B2 protein may result in production of various immunological or other medical reactions which may be diagnostic of abnormal physiological states, e.g., in cell growth, activation, or differentiation.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled APG04, FDH02, or D1B2 protein is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Many of the aforementioned constituents of the drug screening and the diagnostic assays may be used without modification, or may be modified in a variety of ways. For example, labeling may be achieved by covalently or non-covalently joining a moiety which directly or indirectly provides a detectable signal. In any of these assays, the protein, test compound, APG04, FDH02, or D1B2 protein, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free antigen, or alternatively the bound from the free test compound. The APG04, FDH02, or D1B2 protein can be immobilized on various matrices followed by washing. Suitable matrices include plastic such as an ELISA plate, filters, and beads. Methods of immobilizing the APG04, FDH02, or D1B2 protein to a matrix include, without limitation, direct adhesion to plastic, use of a capture antibody, chemical coupling, and biotin-avidin. The last step in this approach involves the precipitation of ligand/receptor or ligand/antibody complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of an APG04, FDH02, or D1B2 protein. These sequences can be used as probes for detecting levels of the APG04, FDH02, or D1B2 protein message in samples from natural sources, or patients suspected of having an abnormal condition, e.g., immune problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various detectable labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorophores, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out using many conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Proaress in Growth Factor Res.* 1:89–97.

XII. Substrate Identification

Having isolated a protease, methods exist for identifying the target substrate. For example, a candidate substrate can be contacted with an APG04, FDH02, or D1B2 protein in an enzymatic reaction. The resulting cleavage product can be analyzed, e.g., using SDS-PAGE, HPLC, or other forms of separation. The molecular weight of the cleavage product should be compared against the molecular weights of the uncleaved substrate and the APG04, FDH02, or D1B2 protein. The successful candidate substrate will exhibit a shift to a lower molecular weight. Analysis of the substrate should determine what site specificity may exist for the enzyme under the tested conditions.

Alternatively, if the protease acts by transforming an inactive substrate to the active form, the resulting activity can be assayed, e.g., by the result of the activated factor, e.g., proliferation, apoptosis, or activation of a target cell.

The broad scope of this invention is best understood with reference to the following examples, which are not intended to limit the invention to specific embodiments.

EXAMPLES

I. General Methods

Many of the standard methods below are described or referenced, e.g., in Maniatis, et al. (1982) *Molecular Cloning, A Laboratory Manual* Cold Spring Harbor Laboratory, Cold Spring Harbor Press, NY; Sambrook, et al. (1989) *Molecular Cloning: A Laboratory Manual* (2d ed.) Vols. 1–3, CSH Press, NY; Ausubel, et al., *Biology* Greene Publishing Associates, Brooklyn, N.Y.; or Ausubel, et al. (1987 and Supplements) *Current Protocols in Molecular Biology* Wiley/Greene, NY; Innis, et al. (eds.) (1990) *PCR Protocols: A Guide to Methods and Applications* Academic Press, NY. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," *Methods in Enzymology* vol. 182, and other volumes in this series; and manufacturer's literature on use of protein purification products, e.g., Pharmacia, Piscataway, N.J., or Bio-Rad, Richmond, Calif. Combination with recombinant techniques allow fusion to. appropriate segments (epitope tags), e.g., to a FLAG sequence or an equivalent which can be fused, e.g., via a protein-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, NY; and Crowe, et al. (1992) *OIAexpress: The High Level Expression & Protein Purification System* QUIAGEN, Inc., Chatsworth, Calif.

Standard immunological techniques are described, e.g., in Coligan (1991) *Current Protocols in Immunology* Wiley/Greene, NY; and *Methods in Enzymology* volumes. 70, 73, 74, 84, 92, 93, 108, 116, 121, 132, 150, 162, and 163. Assays for neural cell biological activities are described, e.g., in Wouterlood (ed. 1995) *Neuroscience Protocols* modules 10, Elsevier; *Methods in Neurosciences* Academic Press; and *Neuromethods* Humana Press, Totowa, N.J. Methodology of developmental systems is described, e.g., in Meisami (ed.) *Handbook of Human Growth and Developmental Biology* CRC Press; and Chrispeels (ed.) *Molecular Techniques and Approaches in Developmental Biology* Interscience.

Fluorescent activated cell sorting (FACS) analysis is described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Isolation of Human APG04, FDH02, or D1B2 Protein

A clone encoding the human APG04, FDH02, or D1B2 protein is isolated from a natural source by many different possible methods. Given the sequences provided herein, PCR primers or hybridization probes are selected and/or constructed to isolate a nucleic acid, e.g., genomic DNA segments or cDNA reverse transcripts. Appropriate cell sources include human tissues, e.g., brain libraries. Tissue distribution below also suggests source tissues. Genetic and polymorphic or allelic variants are isolated by screening a population of individuals.

PCR based detection is performed by standard methods, preferably using appropriate primers from opposite ends of the coding sequence, but flanking segments might be selected for specific purposes.

Alternatively, hybridization probes are selected. Particular AT or GC contents of probes are selected depending upon the expected homology and mismatching expected. Appropriate stringency conditions are selected to balance an appropriate positive signal to background ratio. Successive washing steps are used to identify clones of greater homology.

Further clones will be isolated, e.g., using an antibody based selection procedure. Standard expression cloning methods are applied including, e.g., FACS staining of membrane associated expression product. The antibodies are used to identify clones producing a recognized protein. Alternatively, antibodies are used to purify an APG04, FDH02, or D1B2 protein, with protein sequencing and standard means to isolate a gene encoding that protein.

Genomic or cDNA sequence based methods will also allow for identification of sequences naturally available, or otherwise, which exhibit homology to the provided sequences.

III. Isolation of Mouse APG04, FDH02, or D1B2 Protein

Similar methods are used as above to isolate an appropriate APG04, FDH02, or D1B2 protein gene. Similar source materials as indicated above are used to isolate natural genes, including genetic, polymorphic, allelic, or strain variants. Species variants are also isolated using similar methods.

IV. Isolation of an Avian APG04, FDH02, or D1B2 Protein Clone

An appropriate avian source is selected as above. Similar methods are utilized to isolate other species variants, though the level of similarity will typically be lower for avian APG04, FDH02, or D1B2 protein as compared to a human to mouse sequence.

V. Expression; Purification; Characterization

With an appropriate clone from above, the coding sequence is inserted into an appropriate expression vector. This may be in a vector specifically selected for a prokaryote, yeast, insect, or higher vertebrate, e.g., mammalian expression system. Standard methods are applied to produce the gene product, preferably as a soluble secreted molecule, but will, in certain instances, also be made as an intracellular protein. Intracellular proteins typically require cell lysis to recover the protein, and insoluble inclusion bodies are a common starting material for further purificiation.

With a clone encoding a vertebrate APG04, FDH02, or D1B2 protein, recombinant production means are used, although natural forms may be purified from appropriate sources. The protein product is purified by standard methods of protein purification, in certain cases, e.g., coupled with immunoaffinity methods. Irmunoaffinity methods are used either as a purification step, as described above, or as a detection assay to determine the partition properties of the protein.

Preferably, the protein is secreted into the medium, and the soluble product is purified from the medium in a soluble form. Standard purification techniques applied to soluble proteins are then applied, with enzyme assays or immunodetection methods useful for following where the protease purifies. Alternatively, as described above, inclusion bodies from prokaryotic expression systems are a useful source of material. Typically, the insoluble protein is solubilized from the inclusion bodies and refolded using standard methods. Purification methods are developed as described above.

In certain embodiments, the protein is made in a eukaryotic cell which glycosylates the protein normally. The purification methods may be affected thereby, as may biological activities. The intact protein can be processed to release the protein domain, probably due to a cleavage event. While recombinant protein appears to be processed, the physiological processes which normally do such in native cells remain to be determined.

The product of the purification method described above is characterized to determine many structural features. Standard physical methods are applied, e.g., amino acid analysis and protein sequencing. The resulting protein is subjected to CD spectroscopy and other spectroscopic methods, e.g., NMR, ESR, mass spectroscopy, etc. The product is characterized to determine its molecular form and size, e.g., using gel chromatography and similar techniques. Understanding of the chromatographic properties will lead to more gentle or efficient purification methods.

Prediction of glycosylation sites may be made, e.g., as reported in Hansen, et al. (1995) *Biochem. J.* 308:801–813.

VI. Preparation of Antibodies Against Vertebrate APG04, FDH02, or D1B2 Protein With protein produced and-purified, as above, animals are immunized to produce antibodies. Polyclonal antiserum may be raised using non-purified antigen, though the resulting serum will exhibit higher background levels. Preferably, the antigen is purified using standard protein purification techniques, including, e.g., affinity chromatography using polyclonal serum indicated above. Presence of specific antibodies is detected using defined synthetic peptide fragments.

Alternatively, polyclonal serum is raised against a purified antigen, purified as indicated above, or using synthetic peptides. A series of overlapping synthetic peptides which encompass all of the full length sequence, if presented to an animal, will produce serum recognizing most linear epitopes on the protein. Such an antiserum is used to affinity purify protein. This purified protein, in turn, may be used to immunize another animal to produce another antiserum preparation.

Standard techniques are used to generate induce monoclonal antibodies to either unpurified antigen, or, preferably, purified antigen.

VII. Cellular and Tissue Distribution

Distribution of the protein or gene products are determined, e.g., using immunohistochemistry with an antibody reagent, as produced above, or by screening for nucleic acids encoding the APG04, FDH02, or D1B2 protein. Either hybridization or PCR methods are used to detect DNA, cDNA, or message content. Histochemistry allows determination of the specific cell types within a tissue which express higher or lower levels of message or DNA. Antibody techniques are useful to quantitate protein in a biological sample, including a liquid or tissue sample. Immunoassays are developed to quantitate protein.

Hybridization techniques were applied to the tissue types in described above with positive or negative results, as indicated. The commercial tissue blots may have more significant cellular contamination from other cells, e.g., from blood or other cells which are in the tissue.

The APG04 protease is related to carboxypeptidases which have a catalytic activity of cleaving aa-lysine or aa-arginine carboxy terminal peptidyl bonds. Physiological and candidate substrates thus will include enkephalin and bradykinins. Note also that many residues in the protease match other proteases, e.g., homologs from GenBank designated X80478, S80565, U01909, X14329, X04411, aebp1, bone 2, P12259C1, P12259C2, P00451C1, P00451C2, and P21956.

The FDH02 protease is related to numerous hemoglobinases. Substrates typically used therefor are hemoglobin, but also studies have used azocasein. Related relatives of the proteases cleave at Asn and synthetic peptides containing Asn are often used as substrates. There is some preferential cleavage with these related portions at asn-aa peptidyl linkages in small substrates, and often substrates such as BOC-Asn-OPHNO2 substrates have been used. The octapeptide ETRNGVEE (SEQ ID NO:7) has also been used. See also Abe, et al. (1993) *J. Biol. Chem.* 268:3525–29, which reports on determination of substrate for such a related protein. The results suggest that this protease may be useful for protein sequencing applications.

The D1B2 protease is related to the mouse MS2 protease domain. Insulin and type IV collagen are likely candidates as substrates, based partly upon its homology to hemorrhagic toxin E, which cleaves Asn3-Gln4, Ser9-His10, Ala14-Leu15 in insulin B chain, and at Tyr14-Gln15 and Ala8-Ser9 in A chain; and type IV collagen at Ala258-Gln259 in alpha-1-IV, and at Gly191-Leu192 in alpha-2-IV. Another like substrate is fibrinogen, based upon similarity to snake venom atrolysin E, which cuts the A alpha, and b beta and gamma chains of the fibrinogen subunits. The protease appears to require a Zn cofactor.

VIII. Structure Activity Relationship

Information on the criticality of particular residues is determined using standard procedures and analysis. Standard mutagenesis analysis is performed, e.g., by generating many different variants at determined positions, e.g., at the positions identified above, and evaluating biological activities of the variants. This may be performed to the extent of determining positions which modify activity, or to focus on specific positions to determine the residues which can be substituted to either retain, block, or modulate biological activity.

Alternatively, analysis of natural variants can indicate what positions tolerate natural mutations. This may result from populational analysis of variation among individuals, or across strains or species. Samples from selected individuals are analyzed, e.g., by PCR analysis and sequencing. This allows evaluation of population polymorphisms.

All references cited herein are incorporated herein by reference to the same extent as if each individual publication or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

SEQUENCE SUBMISSION

SEQ ID NO: 1 is human APG04 nucleotide sequence.
SEQ ID NO: 2 is human APG04 amino acid sequence.
SEQ ID NO: 3 is human FDH02 nucleotide sequence.
SEQ ID NO: 4 is human FDH02 amino acid sequence.
SEQ ID NO: 5 is human D1B2 nucleotide sequence.
SEQ ID NO: 6 is human D1B2 amino acid sequence.

What is claimed is:

1. A binding compound comprising an antigen binding of an antibody site which specifically binds to SEQ ID NO:6.

2. The compound of claim 1, wherein said antigen binding site is:
   a) specifically immunoreactive with a protein of SEQ ID NO:6;
   b) raised against a purified or recombinantly produced SEQ ID NO:6;
   c) comprised of a monoclonal antibody, Fab, or F(ab)2; or
   d) detectably labeled.

3. A method for detecting a polypeptide that specifically binds the binding compound of claim 1 in a biological sample comprising
   a) contacting said binding compound with said biological sample;
   b) incubating said binding compound with said biological sample to form a complex of said binding agent and said polypeptide; and
   c) detecting said complex.

4. The method of claim 3, wherein said biological sample is human, and wherein said binding agent is an antibody.

5. A kit comprising a compound of claim 1, wherein said kit further comprises:
   a) instructional material for the use of said compound; and
   b) segregation of said compound into a container.

6. A pharmaceutical composition comprising a binding compound of claim 1.

* * * * *